United States Patent [19]

Dumas

[11] 4,425,155
[45] Jan. 10, 1984

[54] HERBICIDAL SULFONAMIDE N-OXIDES
[75] Inventor: Donald J. Dumas, Wilmington, Del.
[73] Assignee: E. I. Du Pont de Nemours and Company, Wilmington, Del.
[21] Appl. No.: 401,513
[22] Filed: Jul. 26, 1982
[51] Int. Cl.³ .................. C07D 253/06; A01N 43/64
[52] U.S. Cl. ........................................ 71/93; 544/182
[58] Field of Search ........................... 544/182; 71/93

[56] References Cited
U.S. PATENT DOCUMENTS
4,120,691 10/1978 Levitt ................................ 544/182

Primary Examiner—John M. Ford

[57] ABSTRACT

As-Triazinylaminocarbonylsulfonamide N-oxides are useful as agrichemicals and in particular as herbicides.

30 Claims, No Drawings

HERBICIDAL SULFONAMIDE N-OXIDES

BACKGROUND OF THE INVENTION

This invention relates to as-triazinylaminocarbonyl-sulfonamide N-oxides which are useful as agricultural chemicals and in particular as herbicides.

U.S. Pat. No. 4,127,405 teaches compounds which are useful for controlling weeds in wheat having the formula:

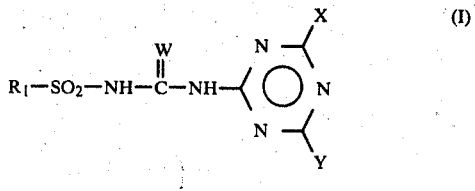

(I)

wherein
$R_1$ is

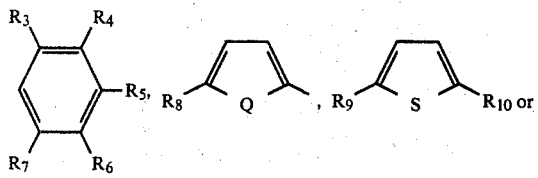

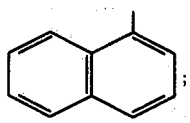

$R_3$ and $R_6$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n$— or $CH_3CH_2S(O)_n$—;
$R_4$ is hydrogen, fluorine, chlorine, bromine or methyl;
$R_5$ is hydrogen, fluorine, chlorine, bromine, methyl or methoxy;
$R_7$ is hydrogen, fluorine, chlorine, bromine, alkyl of 1–2 carbon atoms or alkoxy of 1–2 carbon atom;
$R_8$ is hydrogen, methyl, chlorine or bromine;
$R_9$ and $R_{10}$ are independently hydrogen, methyl, chlorine or bromine;
W and Q are independently oxygen or sulfur;
n is 0, 1 or 2;
X is hydrogen, chlorine, bromine, methyl, ethyl, alkoxy of 1–3 carbon atoms, trifluoromethyl, $CH_3S$— or $CH_3OCH_2$—; and
Y is methyl or methoxy; or their agriculturally suitable salts; provided that:
 (a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;
 (b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and
 (c) when $R_3$ and $R_7$ are both hydrogen, at least one of $R_4$, $R_5$ or $R_6$ must be hydrogen.

French Pat. No. 1,468,747 discloses the following para-substituted phenylsulfonamides, useful as antidiabetic agents:

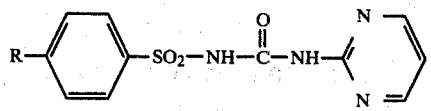

wherein R=H, halogen, $CF_3$ or alkyl.

Logemann et al., Chem. Ab., 53, 18052 g (1959), disclose a number of sulfonamides, including uracil derivatives and those having the formula:

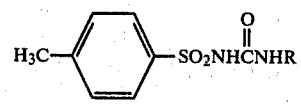

wherein
 R is butyl, phenyl or

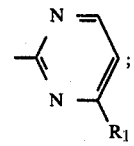

and
 $R_1$ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta, Polon. Pharm. 19, p. 121-5 (1962) [Chem. Ab., 59 1633 e] describes the synthesis of N-[(2,6-dimethoxypyrimidin-4-yl)aminocarbonyl]-4-methylbenzenesulfonamide:

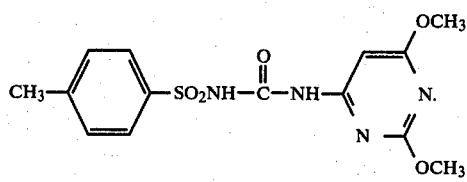

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides,

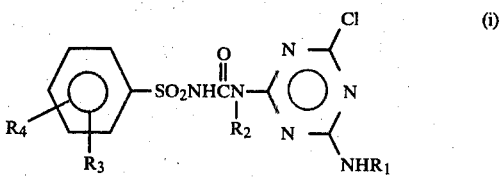

(i)

wherein
 $R_1$ and $R_2$ may independently be alkyl of 1–4 carbon atoms; and
 $R_3$ and $R_4$ may independently be hydrogen, chlorine or alkyl of 1–4 carbon atoms.

Compounds of Formula (ii), and their use as antidiabetic agents, are reported in J. Drug. Res. 6, 123 (1974),

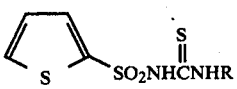 (ii)

wherein R is pyridyl.

The presence of undesired vegetation causes substantial damage to useful crops, especially agricultural products that satisfy man's basic food needs, such as soybeans, barley, wheat, and the like. The current population explosion and concomitant world food shortage demand improvements in the efficiency of producing these crops. Prevention or minimizing the loss of a portion of valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention pertains to novel compounds of Formula I, suitable agricultural compositions containing them, and their method of use as pre-emergent and post-emergent herbicides or plant growth regulants.

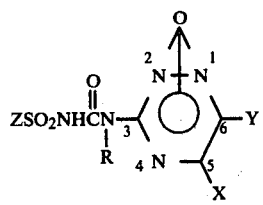 I wherein
Z is

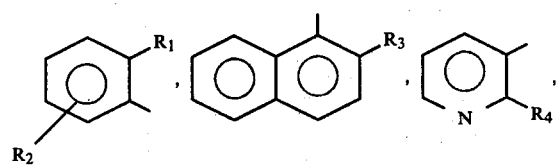

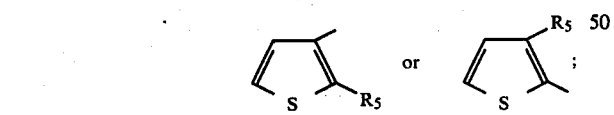

R is H or $CH_3$;
$R_1$ is $CO_2R_6$, $S(O)_nR_7$, $OSO_2R_8$, $OR_9$, $SO_2NR_{10}R_{11}$, $SO_2N(OCH_3)CH_3$, $CH_2OR_{12}$, F, Cl, Br, $NO_2$, $CF_3$ or $C_1-C_4$ alkyl;
$R_2$ is F, Cl, Br, $NO_2$, $CF_3$, $CH_3$, $OCH_3$ or H;
$R_3$ is H, $C_1-C_3$ alkyl, $C_1-C_3$ alkoxy, Cl, $OSO_2CH_3$ or $SO_2R_8$;
$R_4$ is H, $CH_3$, $OCH_3$, Cl, $SO_2CH_3$ or $SO_2N(CH_3)_2$;
$R_5$ is H, $CH_3$, Cl, Br, $NO_2$, $SO_2CH_3$, $SO_2N(CH_3)_2$ or $CO_2R_8$;
$R_6$ is $C_1-C_4$ alkyl, $CH_2CH=CH_2$, $CH_2CH_2OCH_3$ or $CH_2CH_2Cl$;
$R_7$ is $C_1-C_3$ alkyl, $CH_2CH=CH_2$, $CF_3$, $CF_2H$ or $CF_2CF_2H$;
$R_8$ is $C_1-C_3$ alkyl;
$R_9$ is $C_1-C_4$ alkyl, $C_3-C_4$ alkenyl, $CF_3$, $CF_2H$ or $CF_2CF_2H$;
$R_{10}$ and $R_{11}$ are independently $C_1-C_3$ alkyl;
$R_{12}$ is $C_1-C_2$ alkyl;
n is 0, 1 or 2;
X is H, $C_1-C_3$ alkyl, $C_1-C_3$ alkoxy, Cl, Br, $C_1-C_3$ thioalkyl or $N(CH_3)_2$; and
Y is H, Cl, Br, $CH_3$ or $C_2H_5$;
and their agriculturally suitable salts; provided that the total number of carbon atoms in $R_{10}$ and $R_{11}$ are less than or equal to 4.

Preferred for reasons of their higher herbicidal activity and/or more favorable ease of synthesis are:
(1) Compounds of Formula I where the N-oxide is in the 1-position;
Y is H or $CH_3$; and
R is H.
(2) Compounds of Preferred 1 where

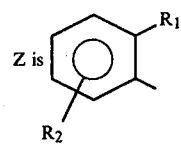

(3) Compounds of Preferred 2 where $R_1$ is $CO_2R_6$, $SO_2NR_{10}R_{11}$, $NO_2$, Cl, $C_1-C_3$ alkyl of $C_1-C_3$ alkoxy.

Specifically Preferred for reasons of their highest herbicidal activity and/or most favorable ease of synthesis are:
2-[(5-methyl-1,2,4-triazin-3-yl)aminocarbonyl-]aminosulfonyl]benzoic acid, methyl ester, 1-oxide;
N-[(5-methyl-1,2,4-triazin-3-yl)aminocarbonyl]-2-chlorobenzenesulfonamide, 1-oxide;
N', N'-dimethyl-N-[(5-methyl-1,2,4-triazin-3-yl)aminocarbonyl]-1,2-benzenedisulfonamide, 1-oxide;
N-[(5-methyl-1,2,4-triazin-3-yl)aminocarbonyl]-2-nitrobenzenesulfonamide, 1-oxide;
N-[(5-methyl-1,2,4-triazin-3-yl)aminocarbonyl]-2-(methylsulfonyloxy)benzenesulfonamide, 1-oxide; and
N-[(5-methyl-1,2,4-triazin-3-yl)aminocarbonyl]-2-propoxybenzenesulfonamide, 1-oxide.

DETAILED DESCRIPTION OF THE INVENTION

Synthesis

Compounds of Formula I are prepared by the general procedure of Equation 1. Z, R, X and Y are as previously defined.

Equation 1

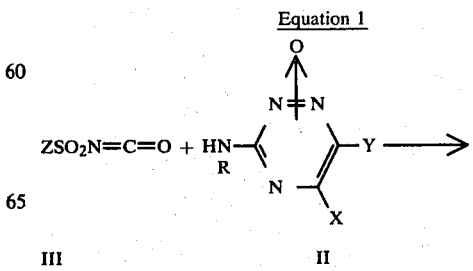

-continued
Equation 1

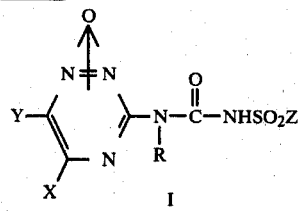

The reaction of Equation 1 is best carried out in an inert aprotic solvent, such as methylene chloride, tetrahydrofuran, or acetonitrile at ambient pressure and temperature. In some cases, the desired product may crystallize from the reaction medium and may be filtered. Reaction products which are soluble in the reaction medium may be isolated by evaporation of the solvent, trituration of the residue with solvents such as diethyl ether, 1-chlorobutane, or hexane. Chromatography (e.g., silica gel) may also be necessary for purification.

Sulfonylisocyanates of Formula III are known in the art and can be prepared by procedures therein. For example, sulfonylisocyanates in which Z is

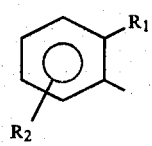

are taught in U.S. Pat. Nos. 4,169,719; 4,127,405; 4,120,691; 4,238,621; European Pat. No. 7687, G.B. No. 2057429A in copending applications U.S. Ser. No. 168,350 and U.S. Ser. No. 168,344; U.S. Ser. No. 227,886 and U.S. Ser. No. 152,021.

Sulfonylisocyanates of Formula III wherein Z is

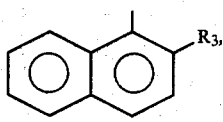

can be prepared by procedures taught in copending application U.S. Ser. No. 184,371.

Sulfonylisocyanates of Formula III wherein Z is

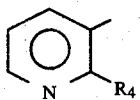

can be prepared by procedures taught in EP No. 13480 and copending application U.S. Ser. No. 128,176.

Sulfonylisocyanates wherein Z is

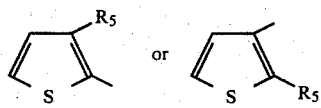

can be prepared by procedures taught in GB No. 2065116A, published June 24, 1981 and copending application U.S. Ser. No. 153,279 and U.S. Ser. No. 247,134.

The intermediate aryl sulfonylisocyanates of Formula III can be prepared by reacting the corresponding aryl sulfonamides with phosgene in the presence of n-butyl isocyanate at reflux in a solvent such as chlorobenzene or xylenes, according to the procedure of H. Ulrich and A. A. Y. Savigh, *Newer Methods of Preparative Organic Chemistry*, Vol. VI, p. 223–241, Academic Press, New York and London, W. Forest Ed., or by the methods taught in U.S. Pat. Nos. 4,127,405 (1978), 4,238,671 (1980) and European Pat. No. 23,141.

The intermediate pyridyl sulfonylisocyanate of Formula III can be prepared by reacting an N-(alkylaminocarbonyl)pyridinesulfonamide with phosgene as described in European Pat. No. 13,480, the disclosure of which is hereby incorporated by reference. The N-(alkylaminocarbonyl)pyridinesulfonamide can be prepared, as described in U.S. Ser. No. 966,258, by the reaction of a pyridinesulfonamide, an alkyl isocyanate and an anhydrous base in an anhydrous solvent.

The thiophene and naphthalene sulfonylisocyanates can be prepared as shown in Equations 2 and 3 respectively, wherein $R_3$ and $R_5$ are as previously defined.

Equation 2

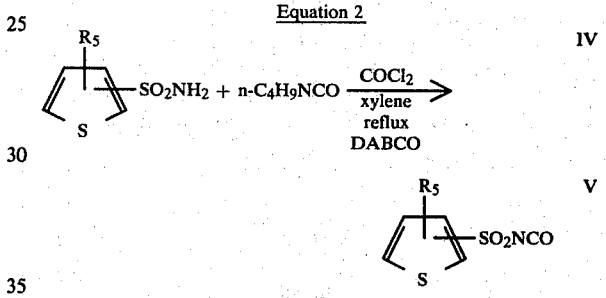

A mixture of the appropriate sulfonamide, e.g., an 2-alkoxycarbonyl-3-thiophene sulfonamide IV such as the methyl ester, an alkyl isocyanate such as butyl isocyanate and a catalytic amount of 1,4-diaza[2.2.2]bicyclooctane (DABCO) in xylene or other inert solvent of sufficiently high boiling point (e.g. >135° C.) is heated to approximately 130°–150° C. Phosgene is added to the mixture until an excess of phosgene is present as indicated by a drop in the boiling point. After the mixture is cooled and filtered to remove a small amount of insoluble by-products, the solvent and alkyl isocyanate are distilled off in vacuo leaving a residue which is the crude sulfonyl isocyanate V.

Equation 3

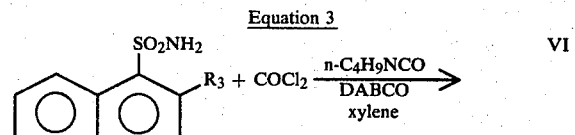

The preparations of naphthalene sulfonylisocyanates VII can be obtained from the corresponding sulfonamide VI. Reaction conditions for the phosgenation would be the same as that for the thiophene sulfonamides in Equation 2.

The preparation of sulfonamides from ammonium hydroxide and sulfonyl chloride is widely reported in the literature, e.g., Crossley et al., *J. Am. Chem. Soc.* 60, 2223 (1938). Certain sulfonyl chlorides are best prepared by chlorosulfonation of a substituted aromatic in carbon tetrachloride according to the teaching of H. T. Clarke et al., *Org. Synth.*, coll. Vol. 1, 2nd Ed., 1941, p. 85. Other benzenesulfonyl chlorides are best made by diazotization of the appropriate aniline with sodium nitrite in HCl, followed by reaction of the diazonium salt with sulfur dioxide and cuprous chloride in acetic acid according to the teaching of H. L. Yale and F. Sowinski, *J. Org. Chem.* 25, 1824 (1960). The preparation of pyridyl sulfonyl chlorides is described in *Chem. Abs.* 88, 190603 m (1978).

Preparations of the aryl sulfonamides are given in U.S. Pat. No. 4,127,405 (1978) wherein $R_1=H$, $C_1-C_4$ alkoxy, F, Cl, Br, $NO_2$, $CF_3$; EPO Publication No. 7687 wherein $R_1=CO_2R_6$; European Pat. No. 23,141 ($R_1=SO_2NR_{10}R_{11}$, $SO_2N(OCH_3)CH_3$); European Pat. No. 23,422 ($R_1=OCF_3$, $OCHF_2$, $OCF_2CF_2H$, $S(O)_nR_7$ where $R_7$ is fluorinated alkyl); European Patent Application No. 44,807 ($S(O)_nR_7$ where $R_7=$allyl); and European Pat. Application 44,808 ($R_7=C_1-C_3$ alkoxy substituted with 1-5 atoms of Cl, Br or F). The synthesis of pyridylsulfonamides is described in G. Machek, *Monatsch* 2, 84 (1939); L. Thunus and C. L. Lapiere, *Ann. Farn.* 33, 663 (1975), and European Pat. No. 13,480.

Equation 4 describes the procedure for making aryl and naphthalene intermediates of Formula VIII when $R_1$ and $R_3$ are $S(O)_nR_7$. The thioether of Formula VIIIb may be prepared from the appropriate 2-aminothiophenol or aminothionaphthalene and an alkyl halide as described in the literature, e.g., R. N. Prasad et al., *Can. J. Chem.* 44, 1247 (1966). The formation of the sulfonamide VIIIc is accomplished in the following manner.

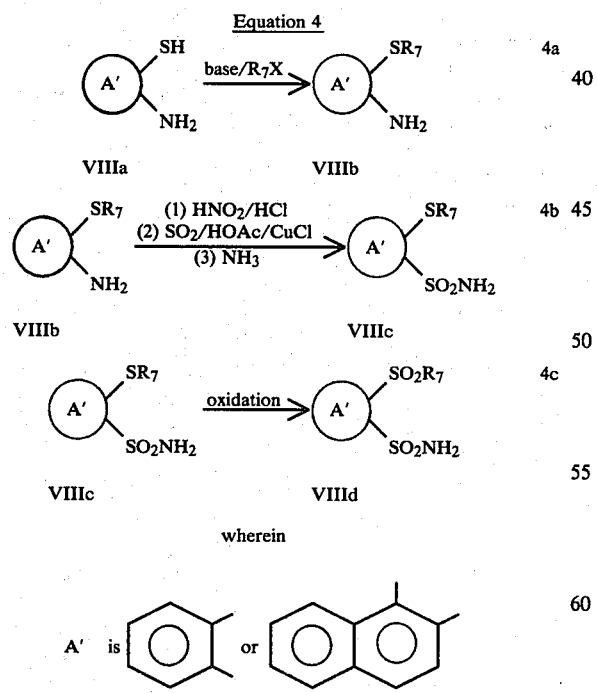

A solution of the thioether of Formula VIIIb in a mixture of concentrated hydrochloric acid and glacial acetic acid is treated with a solution of sodium nitrite in water at $-5°$ to $0°$. After stirring for 10-15 minutes at $0°$ to insure complete diazotization, this solution is added to a mixture of an excess of sulfur dioxide and a catalytic amount of cuprous chloride in glacial acetic acid at $0°-5°$. The temperature is kept at $0°-5°$ for $\frac{1}{4}$ to 1 hour and is then raised to $20°-25°$ and held at that temperature for 2-4 hours. This solution is then poured into a large excess of ice water. The sulfonyl chloride products can be isolated by filtration or by extraction into solvent such as ethyl ether or methylene chloride followed by evaporation of the solvent.

The amination described in step (4b) is conveniently carried out by treating a solution of the sulfonyl chloride with an excess of anhydrous ammonia in a solvent such as ethyl ether or methylene chloride at $0°-25°$. If the product sulfonamide is insoluble it may be isolated by filtration followed by washing out the salts with water. If the product sulfonamide is soluble in the reaction solution, it may be isolated by filtering off the precipitated ammonium chloride and evaporating the solvent.

Sulfonamides of Formula VIIIc wherein A'=aryl may also be prepared from the appropriate chlorobenzenesulfonamides (synthesis taught in U.S. Pat. No. 4,127,405) as shown in Equation 5. Heating an equimolar mixture of the appropriate sulfonamide and mercaptan in the presence of two equivalents of base will yield VIIIc following acidic work-up. As in Equation 4, the sulfonamides VIIId can be prepared by oxidation of VIIIc.

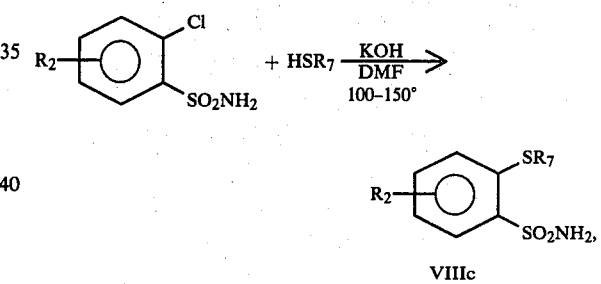

Synthesis of thiophene sulfonamides of Formula IXe and IXf may be accomplished by the method outlined in Equation 6. The sulfonyl chlorides of Formula IXa are described by H. D. Hartough in "The Chemistry of Heterocyclic Compounds," v. 3, Interscience Publishers, Inc., N.Y. 1952. These may be converted to the corresponding N-t-butyl sulfonamides IXb by admixture with at least twice the equivalent amount of t-butylamine in an inert solvent, such as ether, filtration of the amine hydrochloride, and evaporation of the solvent. The lithiation of thiophenes and of aromatic N-t-butylsulfonamides with n-butyllithium, t-butyllithium, lithium diisopropylamide and lithium 2,2,6,6-tetramethyl piperidide is reviewed by H. W. Gschwend and H. R. Rodriguez in *Org. React.*, 26, 1 (1979), and is generally carried out by cooling to $-78°$ a solution of twice the equimolar amount of base kept under an inert atmosphere, in an ethereal solvent such as diethyl ether or THF, and adding a solution of the compound of Formula IXb. The compounds of Formula IXc may be prepared as shown in Equation (6b) by adding an equimolar quantity of the dimethyl disulfide, allowing the mixture to warm to room temperature, washing the mixture with acidic brine, and evaporation of the solvent.

Equation 6

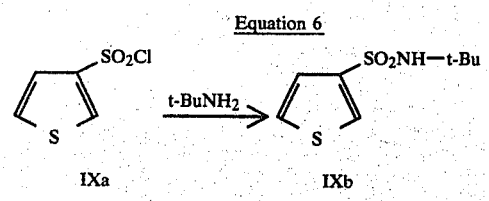

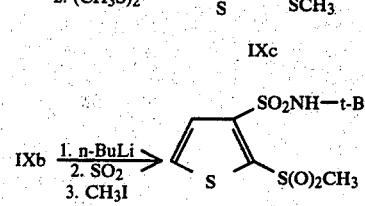

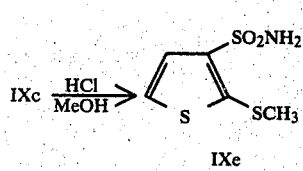

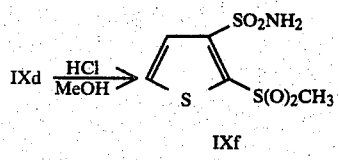

Alternatively, as shown in Equation (6c), in order to prepare the compounds of Formula IXd, the lithiation mixture may be treated with an equimolar quantity of sulfur dioxide, allowing the mixture to warm to room temperature, filtration of the solid precipitate, dissolution of this salt in ethanol and adding an equimolar amount of methyl iodide. This alkylation step may be carried out at temperatures of 25° to 78°. The cooled reaction mixture may be diluted with dilute aqueous hydrochloric acid to precipitate the product IXd. The t-butyl sulfonamides of Formula IXc and IXd may be converted to the compounds of Formula IXe and IXf, respectively, by heating in methanol containing at least an equimolar quantity of hydrochloric acid, followed by concentration of the reaction mixture and precipitation of the product with ether.

An alternate preparation of the thiophene sulfonamides of Formula IXf is described in Equation 7.

Equation 7

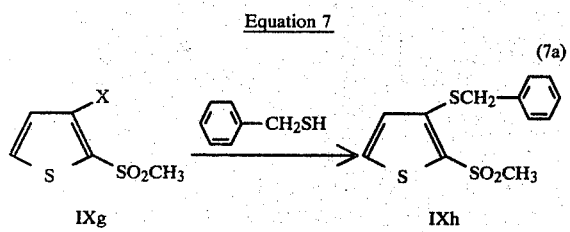

-continued
Equation 7

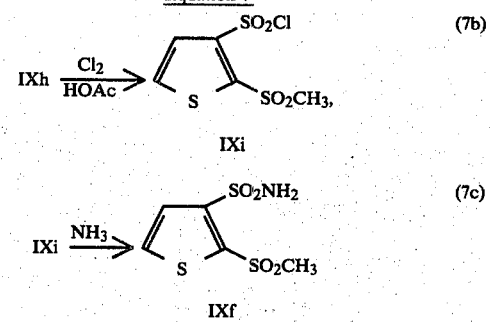

wherein X=Cl or Br.

The reaction of Equation (7a) is accomplished by mixing equimolar quantities of the appropriate halide IXg with an equimolar quantity of benzyl mercaptan in a polar solvent, such as dimethylformamide, containing an equimolar amount of a strong base, such as sodium methoxide or sodium hydride, heating at a temperature between 50° and 120°, and isolating the product by precipitation with ice-water and washing with hexane. The sulfides of Formula IXh are converted to the sulfonyl chlorides IXi as shown in Equation (7b) by contacting with at least three equivalents of chlorine in acetic acid according to the procedure of R. F. Langler, Can. J. Chem., 54, 498 (1976). The sulfonyl chlorides can be precipitated by the addition of ice-water to the chlorination mixture. Ammonolysis of thiophene sulfonyl chlorides gives IXf.

Compounds of Formulae Xb (Equation 8) may be prepared by adding twice the equimolar amount of chlorosulfonic acid, diluted in an inert solvent, such as dichloromethane, to the appropriate 3-thienyl sulfide Xa at temperature between −30° and 25°, washing the mixture with ice-water and evaporating the solvent. These may be converted to the appropriate compounds of Formula Xc by treatment with ammonia. The sulfides of Formula Xc may be oxidized to compounds of Formula Xd.

Equation 8

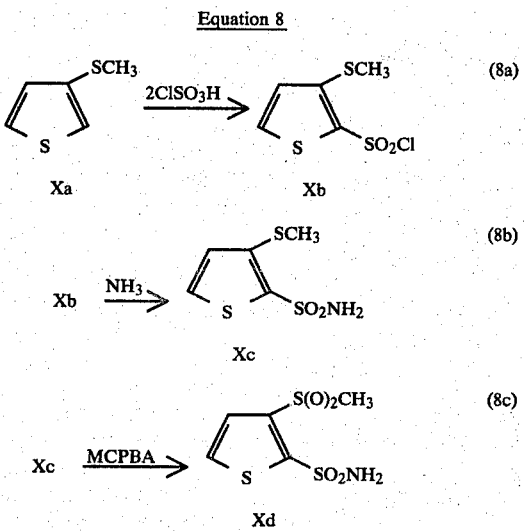

Also, the methods described in Equation 6 may be applied in making compounds of Formula Xd.

According to the method outlined in Equation 9, compounds of Formulae XIb, wherein X=chlorine or bromine can be prepared from sulfonyl chlorides of Formula XIa by ammonolysis.

Equation 9

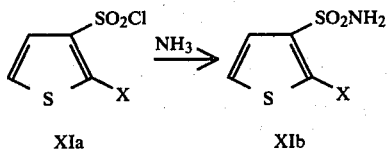

XIa          XIb

Precursors to the required thiophene sulfonyl chlorides and sulfonamides are prepared by a variety of synthetic routes depending on the chemical properties of the substituent and its position on the thiophene ring.

Direct sulfonation or chlorosulfonation to sulfonic acid or sulfonyl chloride derivatives can be carried out according to the references cited in "Thiophene and its Derivatives," H. D. Hartough, Interscience, New York, 1952. The structure of sulfonation products of 3-alkyl thiophenes has been reported as uncertain. Nuclear magnetic resonance studies indicate the chlorosulfonation occurs predominantly at the 2- rather than the 5-position.

Sulfonic acids are readily converted to sulfonyl chlorides, using methods well known in the art, by chlorinating agents such as phosphorus pentachloride, phosphorus oxychloride or thionyl chloride. A mixture of sulfonyl chloride in dimethylformamide can also be used to prepare thiophenesulfonyl chlorides of active thiophene intermediates according to the method of E. Testa et al., Helv. Chim. Acta., 47, 766 (1963).

Other intermediates can be prepared via lithiation reactions. A review of this chemistry appears in Organic Reactions, Vol. 26., Gschwind, H. W. and Rodriguez, H. R., John Wiley and Sons, Inc., New York, 1979. Examples of the application of this chemistry to the preparation of intermediates used here is shown in the following equations.

Equation 10 shows the preparation of sulfamyl thiophene sulfonamides via lithiated intermediates.

Equation 10

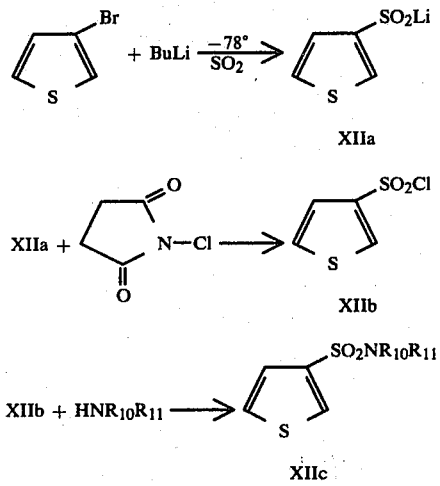

-continued
Equation 10

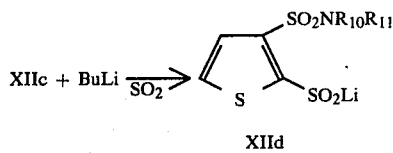

XIId

As shown in Equation 10, 3-bromothiophene is converted to 3-lithiothiophene at −78° in an inert solvent such as tetrahydrofuran and the mixture is then contacted with sulfur dioxide. The resultant lithio sulfinate is stirred at room temperature in acetic acid or aqueous 2-propanol with N-chlorosuccinimide to yield the 3-thiophenesulfonyl chloride XIIb. This product is then contacted with an amine, $HNR_{10}R_{11}$ wherein $R_{10}$ and $R_{11}$ are as previously defined. The 3-thiophenesulfonamide XIIc, thus formed is reacted with butyl lithium at −40° to 0° C. followed by sulfur dioxide to form the lithio 3-sulfamyl-2-thiophenesulfinate XIId which is converted to the sulfonyl chloride as described above. Conversion of this sulfonyl chloride to the sulfonamide and sulfonylisocyanate is carried out as previously described.

Disulfides such as structure XV, reported by Henriksen and Autruys, Acta. Chem. Scands., 24 2629 (1970), are also useful intermediates for conversion to sulfonyl chlorides as shown in Equation 11.

Equation 11

$$\left[ \begin{array}{c} \diagdown\!\!\!\!\diagup\!\!\!\!-\!NO_2 \\ S \end{array} \!\!-\!S\!- \right]_2 + Cl_2 \longrightarrow \begin{array}{c} \diagdown\!\!\!\!\diagup\!\!\!\!-\!NO_2 \\ S \quad SO_2Cl \end{array}$$

XIII          XIV

The disulfide intermediate XIII is converted to the sulfonyl chloride XIV by passing chlorine gas into aqueous hydrochloric or acetic acid solution or suspension of XIV.

Alternatively, the diazotization reaction of thiophene amines to sulfonyl chlorides such as structure XV shown in Equation 12 are carried out according to the general procedure of H. L. Yale and F. Sowinski, J. Org. Chem., 25, 1824 (1960).

Equation 12

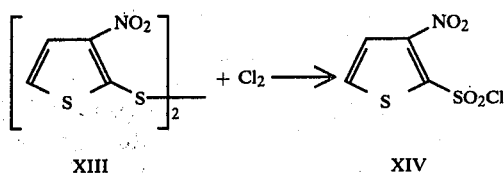

XV          XVa

The o-alkoxymethyl nitrobenzenes XVIb are in turn prepared via "Williamson Synthesis", according to Equation 13a or 13b.

Equation 13a

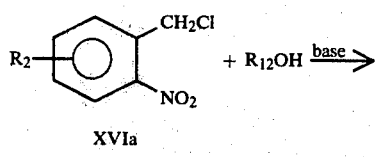

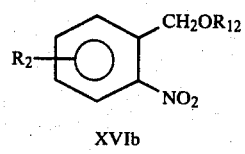

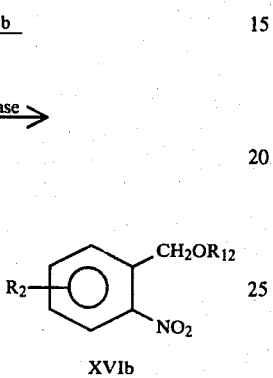

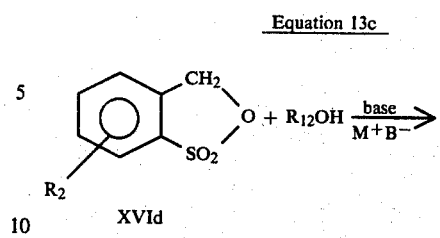

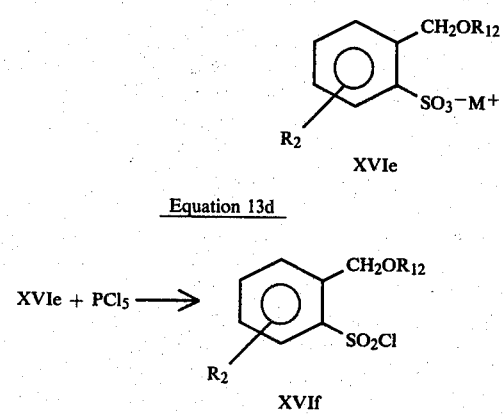

"Williamson Synthesis" has been widely used for the preparation of ethers as reviewed by W. Theilheimer, *Syn. Methods of Org. Chem.*, Vol. VII, p. 112.

Alternatively, o-alkoxymethyl methylbenzenesulfonyl chlorides, XVIf, can be obtained from an appropriately substituted α-hydroxy-o-toluenesulfonic acid-α-sultone, XVId, via ring-opening reaction with an alkoxide anion as depicted in Equations 13c and 13d.

Reaction 13c is closely related to the alkylation of acyloxides and acetamide with sultones as disclosed by J. H. Helberger et al., Ann., 565 22 (1949). Conversion of the sulfonic acid salts to the sulfonyl chloride is then carried out according to the teaching of *Org. Synthesis*, Coll. Vol. IV, 846, 693.

Benzenesulfonamides of Formula XVIIb can also be derived from compound XVIIa as illustrated in Equation 14.

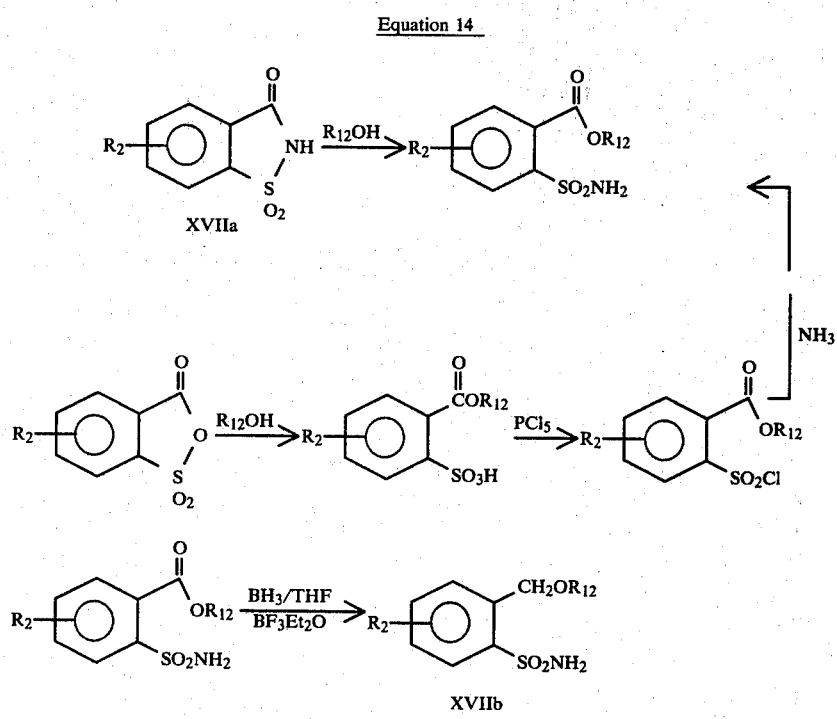

Preparation of o-sulfamylbenzoic acid esters, from saccharin or sulfobenzoic acid anhydride is well known in the art, e.g., B. Loev and M. Kormendy, *J Org. Chem.*

27, 1703 (1962). The esters can be readily reduced to the ethers with diborane in a suitable organic solvent, e.g., tetrahydrofuran, in the presence of fifteen fold of boron trifluoride etherate under reflux for 18 hours, as described by R. P. Graber and M. B. Meyers, *J. Org. Chem.*, 26, 4773 (1961).

Most generally, the napthalene sulfonamides may be prepared from the sulfonyl chlorides XVIIIb (Equation 15) as described in "Preparative Organic Chemistry", ed. G. Hilgetag and A. Martini, J. Wiley and Sons, New York (1972). The sulfonyl chlorides may be prepared by chlorination of the sulfonic acids XXIa by methods described by Hilgetag and Martini, op. cit. The preparation of these acids is described in the art. These compounds may be further transferred by methods known in the art to yield other disclosed sulfonic acids.

Equation 15

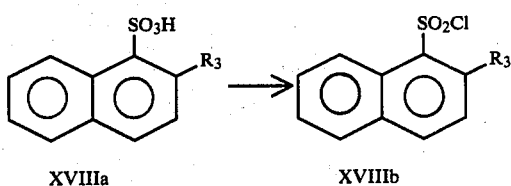

Procedures for the preparation of 3-amino-as-triazines and their N-oxides are well known in the art. A general review is available in H. Neuhoeffer and P. F. Wiley, "Chemistry of 1,2,3-Triazines and 1,2,4-Triazines, Tetrazines, and Pentazines" in "The Chemistry of Heterocyclic Compounds", A. Weissberger and E. C. Taylor, editors, Wiley 1978.

Two alternatives for the synthesis of alkyl or dialkyl-3-amino-as-triazine 1-oxides are available depending on the relative steric bulk of the substituents at C5 and C6. When X is of equal or greater steric bulk than Y, the compounds may best be prepared by the method described by W. W. Paudler and T.-K. Chen in *J. Org. Chem.*, 36, 787 (1971) and *J. Heterocycl. Chem.*, 7, 767 (1970) as outlined in Equation 16.

Equation 16

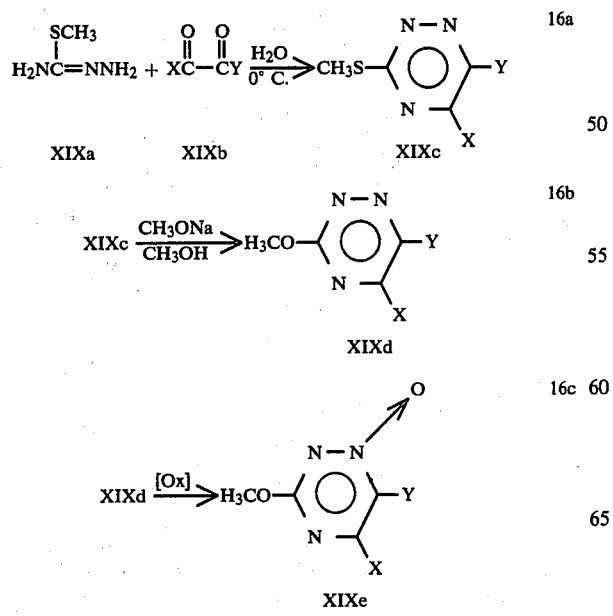

-continued
Equation 16

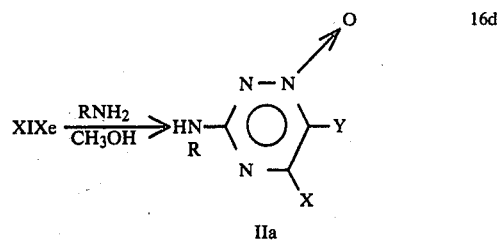

X is H, $C_1$–$C_3$ alkyl; and
Y is H, $C_1$–$C_2$ alkyl.

Condensation of S-methylthiosemicarbazide (XIXa) with an appropriate 1,2-dicarbonyl compound (XIXb) in aqueous solution at 0°–25° C. gives XIXc which in turn is converted to XIXd by reaction with sodium methoxide in methanol at ambient temperature. Reaction of XIXd with an appropriate oxidizing agent, e.g., MCPBA, in a suitable solvent, e.g., $CH_2Cl_2$, at ambient temperature gives triazine 1-oxide XIXe which is converted to IIa on exposure to $NH_3$ or $CH_3NH_2$ in an appropriate solvent, e.g., methanol at a temperature up to 100° C. in a sealed vessel.

When Y is of greater steric bulk than X, the compounds may be prepared by the procedure of M. Bobek, M. Glowka, and R. Parthasarathy in *J. Org. Chem.*, 47, 913 (1982) as described in Equation 17.

Equation 17

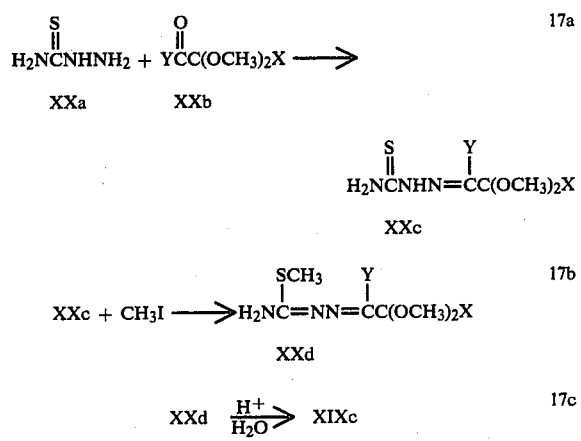

X is H, $CH_3$; and
Y is $C_1$–$C_2$ alkyl.

Reaction of thiosemicarbazide (XXa) with an appropriate monoacetal (or monoketal) XXb in a suitable solvent, e.g., methanol, at reflux for 10–20 minutes gives hydrazone XXc. Reaction of XXc with methyl iodide in a suitable solvent, e.g., methanol, at 5° to 50° C. for 2–4 hours provides XXd which on acid hydrolysis at 55°–60° C. for 1–3 hours gives XIXc. The product is converted to IIa as shown in Equation 16.

3-Amino-as-triazine 2-oxides IIb wherein X is H or $C_1$–$C_3$ alkyl and Y is H, $CH_3$ or $C_2H_5$ can be prepared as described in Equation 18.

Equation 18

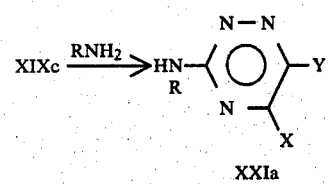
18a

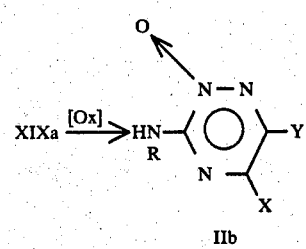
IIb 18b

Reaction of XIXc with NH$_3$ or CH$_3$NH$_2$ in an appropriate solvent, e.g., methanol, at a temperature up to 100° C. in a sealed vessel results in 3-amino-as-triazines XXIa. Reaction of XXIa with an appropriate oxidizing agent, e.g., MCPBA, in a suitable solvent, e.g., CH$_3$CN, at 20° C. to reflux according to the method described by R. J. Radel, B. T. Keen, C. Wong and W. W. Paudler in J. Org. Chem., 42, 546 (1977) results in 3-amino-as-triazine 2-oxides.

3-Amino-as-triazine 4-oxides IIc wherein X is H or C$_1$–C$_3$ alkyl and Y is H, CH$_3$ or C$_2$H$_5$ can be prepared by the methods described by F. L. Scott and J. Reilly in Chem. and Ind., (London) 907 (1952) and outlined in Equation 19.

Equation 19

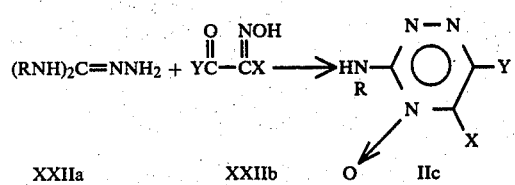

Reaction of XXIa with the appropriate α-oximinocarbonyl compound in a suitable solvent, e.g. acetic acid, at 0° C. to reflux temperature gives compound IIc.

3-Amino-5-halo-as-triazine 1-oxides (IIa, wherein X=Br or Cl) may be prepared from the corresponding 3-amino-as-triazines XXIa, wherein X is H and Y is H, CH$_3$ or C$_2$H$_5$, as shown in Equation 20.

Equation 20

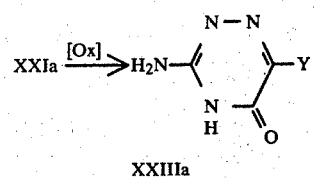
XXIIIa 20a

-continued
Equation 20

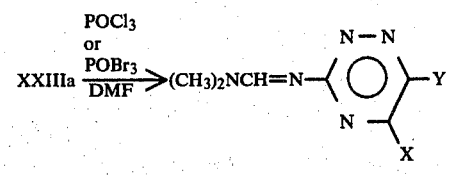
XXIIIb  X = Br, Cl 20b

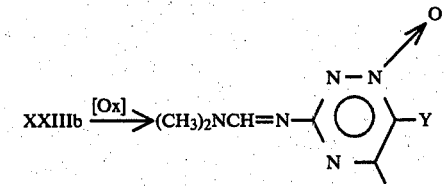
XXIIIc  X = Br, Cl 20c

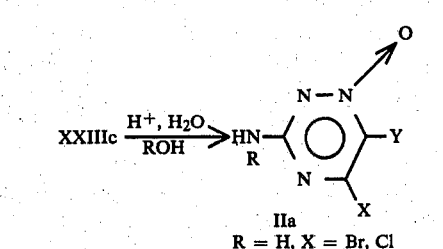
IIa
R = H, X = Br, Cl 20d

Compounds XXIIIa may be prepared by the method of T. Sasaki and K. Minamoto in Chem. Pharm. Bull., 12, 1329 (1964). Treatment of XXIa with an appropriate oxidizing agent, e.g., H$_2$O$_2$, in a suitable solvent, e.g., acetic acid, at 25°–50° C. gives as-triazinones XXIIIa. Reaction of XXIIIa with an excess of POCl$_3$ or POBr$_3$ in DMR at 25° C. to reflux temperature results in 3-amidino-5-halo-as-triazines XXIIIb. Treatment of XXIIIb with an appropriate oxidizing, e.g., MCPBA, in a suitable solvent, e.g., CH$_2$Cl$_2$, at ambient to reflux temperature gives as-triazine 1-oxides XXIIIc. Compounds XXIIIc may be converted to the 3-amino compounds IIa on exposure to aqueous methanol and a suitable acid catalyst, e.g., PTSA, at ambient temperature.

3-Amino-5-halo-as-triazines 2-oxides (IIb, wherein X=Br or Cl) may be prepared from the corresponding 3-amino-5-oxo-as-triazines XXIIIa, wherein Y is H, CH$_3$ or C$_2$H$_5$, as shown in Equation 21.

Equation 21

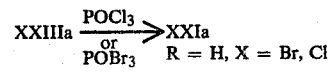
21a

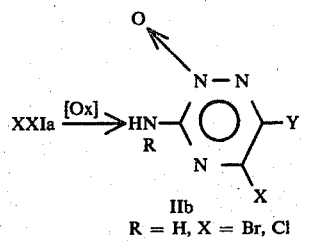
IIb
R = H, X = Br, Cl 21b

Reaction of XXIIIa with POCl$_3$ or POBr$_3$ at 20° C. to reflux temperature gives 5-halo derivatives XXIa which can then be converted to IIb by oxidation as described in Equation 18.

3-Amino-5-halotriazine 4-oxides IIc (X=Br, Cl) can be prepared from compounds IIc wherein X is H as shown in Equation 22.

Equation 22

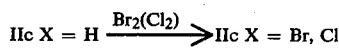

Reaction of IIc wherein X is H with Br$_2$ or Cl$_2$ in an appropriate solvent, e.g., CCl$_4$, in the presence of a suitable acid scavenger, e.g., K$_2$CO$_3$, at 20°–50° C. gives IIc wherein X is Br or Cl.

3-Amino-as-triazine N-oxides IIa,b wherein R is H can be converted to the corresponding 3-aminomethyl compounds by reaction with CH$_3$I in an appropriate solvent, e.g., acetone, in the presence of a suitable acid scavenger, e.g., K$_2$CO$_3$, as shown in Equation 23.

Equation 23

| IIa,b | | IIa,b |
|---|---|---|
| R = H | CH$_3$I $\rightarrow$ | R = CH$_3$ |

Compounds IIa,b,c wherein X is Br or Cl and Y is H, CH$_3$, C$_2$H$_5$ may be converted to the corresponding 5-alkoxy, 5-thioalkyl, and 5-dimethylamino derivatives by treatment with an appropriate nucleophile in a suitable solvent, e.g., CH$_3$ONa/CH$_3$OH, KSCH$_3$/DMF, HNMe$_2$/DMF, as shown in Equation 24.

Equation 24

| IIa,b,c | | IIa,b,c |
|---|---|---|
| X = Br, Cl<br>Y = H, CH$_3$ or C$_2$H$_5$ | :Nu $\rightarrow$ | X = C$_1$–C$_3$ alkoxy,<br>C$_1$–C$_3$ thioalkyl<br>or N(CH$_3$)$_2$;<br>Y = H, CH$_3$ or C$_2$H$_5$. |

3-Amino-6-halo-as-triazine N-oxides IIa,b,c, wherein Y is Br or Cl may be prepared from compounds IIa,b,c wherein Y is H by the methods of B. T. Keen, R. J. Radel, and W. W. Paudler in *J. Org. Chem.*, 42, 3498 (1977) as described in Equation 25.

Equation 25

| IIa,b,c | | IIa,b,c |
|---|---|---|
| Y = H | Br$_2$(Cl$_2$) $\rightarrow$ | Y = Br, Cl |

Halogenation with Br$_2$ or Cl$_2$ in an appropriate solvent, e.g., CCl$_4$, in the presence of a suitable acid scavenger, e.g., K$_2$CO$_3$, at 20°–50° C. gives the 6-halo derivatives.

EXAMPLE 1

Preparation of 3-Amino-5-methyl-1,2,4-triazine 1-Oxide (1)

To a slurry of 5.1 g (0.036 mol) of 3-methoxy-5-methyl-1,2,4-triazine 1-oxide (prepared by the procedure of W. W. Paudler and T.-K. Chen in *J. Org. Chem.*, 36, 789 (1971)) was added a solution of 10 ml of ammonia in 50 ml of methanol. The resulting solution was stored in a loosely stoppered flask for 66 hours. The crystals which formed were collected by filtration, washed with methanol, and dried under vacuum at ambient temperature to afford 3.3 g of 1 as shiny off-white plates, m.p. 279° C.(d). Retreatment of the mother liquors with an additional 5 ml of ammonia provided a second crop of 0.9 g, m.p. 272°–273° C.(d).

NMR: δ2.25 (s, CH$_3$); 7.13 (br s, NH$_2$); and 7.67 (s, C-6-H).

EXAMPLE 2

Preparation of 2-[[(5-methyl-1,2,4-triazin-3-yl)aminocarbonyl]aminosulfonyl]benzoic acid, methyl ester, 1-Oxide (2)

A mixture of 1.06 g (0.0044 mol) of 2-(methoxycarbonyl)benzenesulfonyl isocyanate (prepared according to the procedure in U.S. Pat. No. 4,238,621), 0.50 g (0.0040 mmol) of 1, and 20 ml of acetonitrile was stirred at ambient temperature for 48 hours. The precipitate was filtered and washed successively with acetonitrile and n-butyl chloride, then dried under vacuum at 60° C. to afford 0.8 g of 2 as a white solid, m.p. 199°–201° C.(d).

NMR: δ2.5 (s, CH$_3$); 3.9 (s, CO$_2$CH$_3$); 7.7–8.4 (m, ArH, NH); and 11.0 (br s, NH).

Using the procedure of Example 2, the following compounds may be prepared by one skilled in the art.

TABLE I

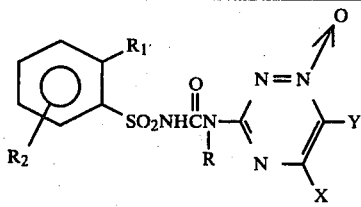

| R$_1$ | R | R$_2$ | X | Y | m.p. (°C.) |
|---|---|---|---|---|---|
| CO$_2$CH$_3$ | H | H | CH$_3$ | H | 199–201° (d) |
| CO$_2$CH$_2$CH$_3$ | H | H | CH$_3$ | H | 169–171° (d) |
| CO$_2$CH$_2$CH$_2$CH$_3$ | H | H | CH$_3$ | H | 149–153° (d) |
| CO$_2$CH(CH$_3$)$_2$ | H | H | CH$_3$ | H | 173–175° (d) |
| CO$_2$CH$_2$CH$_2$CH$_2$CH$_3$ | H | H | CH$_3$ | H | |
| CO$_2$CH$_2$CH=CH$_2$ | H | H | CH$_3$ | H | |
| CO$_2$CH$_2$CH$_2$OCH$_3$ | H | H | CH$_3$ | H | |
| CO$_2$CH$_2$CH$_2$Cl | H | H | CH$_3$ | H | |
| SCH$_3$ | H | H | CH$_3$ | H | |
| SCH$_2$CH$_3$ | H | H | CH$_3$ | H | |
| SCH(CH$_3$)$_2$ | H | H | CH$_3$ | H | |

TABLE I-continued

| R₁ | R | R₂ | X | Y | m.p. (°C.) |
|---|---|---|---|---|---|
| SCH₂CH=CH₂ | H | H | CH₃ | H | |
| SCF₃ | H | H | CH₃ | H | |
| SCF₂H | H | H | CH₃ | H | |
| SOCH₃ | H | H | CH₃ | H | |
| SOCH₂CH₃ | H | H | CH₃ | H | |
| SOCH(CH₃)₂ | H | H | CH₃ | H | |
| SOCH₂CH=CH₂ | H | H | CH₃ | H | |
| SOCF₃ | H | H | CH₃ | H | |
| SOCF₂H | H | H | CH₃ | H | |
| SOCF₂CF₂H | H | H | CH₃ | H | |
| SO₂CH₃ | H | H | CH₃ | H | 192–193° (d) |
| SO₂CH₂CH₃ | H | H | CH₃ | H | |
| SO₂CH(CH₃)₂ | H | H | CH₃ | H | |
| SO₂CH₂CH=CH₂ | H | H | CH₃ | H | |
| SO₂CF₃ | H | H | CH₃ | H | |
| SO₂CF₂H | H | H | CH₃ | H | |
| SO₂CF₂CF₂H | H | H | CH₃ | H | |
| OSO₂CH₃ | H | H | CH₃ | H | 197–200° (d) |
| OSO₂CH₂CH₃ | H | H | CH₃ | H | |
| OSO₂CH(CH₃)₂ | H | H | CH₃ | H | |
| OCH₃ | H | H | CH₃ | H | |
| OCH₂CH₃ | H | H | CH₃ | H | |
| OCH₂CH₂CH₃ | H | H | CH₃ | H | 181–184° (d) |
| OCH(CH₃)CH₂CH₃ | H | H | CH₃ | H | |
| OCH₂CH=CH₂ | H | H | CH₃ | H | |
| OCH₂CH₂CH=CH₂ | H | H | CH₃ | H | |
| OCH(CH₃)CH=CH₂ | H | H | CH₃ | H | |
| SO₂N(CH₃)₂ | H | H | CH₃ | H | 202–206° (d) |
| SO₂N(CH₃)CH(CH₃)₂ | H | H | CH₃ | H | |
| SO₂N(OCH₃)CH₃ | H | H | CH₃ | H | |
| CH₂OCH₃ | H | H | CH₃ | H | |
| CH₂CH₂OCH₃ | H | H | CH₃ | H | |
| F | H | H | CH₃ | H | |
| Cl | H | H | CH₃ | H | 206–207° (d) |
| Br | H | H | CH₃ | H | |
| NO₂ | H | H | CH₃ | H | 199–201° (d) |
| CF₃ | H | H | CH₃ | H | |
| CH₃ | H | H | CH₃ | H | |
| CH₂CH₃ | H | H | CH₃ | H | |
| CH(CH₃)₂ | H | H | CH₃ | H | |
| CH₂CH₂CH₂CH₃ | H | H | CH₃ | H | |
| CO₂CH₃ | CH₃ | H | CH₃ | H | |
| SCH₃ | CH₃ | H | CH₃ | H | |
| SCF₃ | CH₃ | H | CH₃ | H | |
| SOCH₃ | CH₃ | H | CH₃ | H | |
| SOCF₃ | CH₃ | H | CH₃ | H | |
| SO₂CH₃ | CH₃ | H | CH₃ | H | |
| SO₂CF₃ | CH₃ | H | CH₃ | H | |
| OSO₂CH₃ | CH₃ | H | CH₃ | H | |
| OCH₃ | CH₃ | H | CH₃ | H | |
| SO₂N(CH₃)₂ | CH₃ | H | CH₃ | H | |
| SO₂N(OCH₃)CH₃ | CH₃ | H | CH₃ | H | |
| CH₂OCH₃ | CH₃ | H | CH₃ | H | |
| CH₂CH₂OCH₃ | CH₃ | H | CH₃ | H | |
| Cl | CH₃ | H | CH₃ | H | |
| NO₂ | CH₃ | H | CH₃ | H | |
| CF₃ | CH₃ | H | CH₃ | H | |
| CH₃ | CH₃ | H | CH₃ | H | |
| NO₂ | H | 5-CF₃ | CH₃ | H | |
| NO₂ | H | 3-Cl | CH₃ | H | |
| Cl | H | 6-NO₂ | CH₃ | H | |
| CF₃ | H | 5-NO₂ | CH₃ | H | |
| Cl | H | 5-Cl | CH₃ | H | |
| NO₂ | H | 5-Cl | CH₃ | H | |
| SO₂N(CH₃)₂ | H | 3-Cl | CH₃ | H | |
| CO₂CH₃ | H | 5-CH₃ | CH₃ | H | |
| Cl | H | 3-Br | CH₃ | H | |
| Cl | H | 5-Br | CH₃ | H | |
| NO₂ | H | 6-F | CH₃ | H | |
| Cl | H | 6-F | CH₃ | H | |

TABLE I-continued

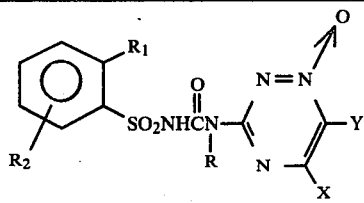

| R₁ | R | R₂ | X | Y | m.p. (°C.) |
|---|---|---|---|---|---|
| Br | H | 3-F | CH₃ | H | |
| NO₂ | CH₃ | 5-NO₂ | CH₃ | H | |
| CO₂CH₃ | CH₃ | 3-OCH₃ | CH₃ | H | |
| CH₃ | CH₃ | 3-NO₂ | CH₃ | H | |
| CO₂CH₃ | H | H | CH₃ | Cl | |
| NO₂ | H | H | CH₃ | Cl | |
| Cl | H | H | CH₃ | Cl | |
| OCH₂CH₂CH₃ | H | H | CH₃ | Cl | |
| SO₂N(CH₃)₂ | H | H | CH₃ | Cl | |
| CO₂CH₃ | CH₃ | H | CH₃ | Cl | |
| CO₂CH₃ | H | 5-CF₃ | CH₃ | Cl | |
| NO₂ | CH₃ | 5-Cl | CH₃ | Cl | |
| CO₂CH₃ | H | H | CH₃ | Br | |
| NO₂ | H | H | CH₃ | Br | |
| Cl | H | H | CH₃ | Br | |
| CO₂CH₃ | H | 5-OCH₃ | CH₃ | Br | |
| CO₂CH₃ | CH₃ | H | CH₃ | Br | |
| CO₂CH₃ | H | H | CH₃ | C₂H₅ | |
| NO₂ | H | H | CH₃ | C₂H₅ | |
| SO₂N(CH₃)₂ | H | 3-Cl | CH₃ | C₂H₅ | |
| OCH₂CH₂CH₃ | H | H | CH₃ | C₂H₅ | |
| CO₂CH₃ | CH₃ | H | CH₃ | C₂H₅ | |
| CO₂CH₃ | H | H | C₂H₅ | H | |
| SO₂CH₃ | H | H | C₂H₅ | H | |
| OSO₂CH₃ | H | H | C₂H₅ | H | |
| OCH₂CH₂CH₃ | H | H | C₂H₅ | H | |
| CH₂OCH₃ | H | H | C₂H₅ | H | |
| CH₂CH₂OCH₃ | H | H | C₂H₅ | H | |
| Cl | H | H | C₂H₅ | H | |
| NO₂ | H | H | C₂H₅ | H | |
| CF₃ | H | H | C₂H₅ | H | |
| CO₂CH₃ | CH₃ | H | C₂H₅ | H | |
| CO₂CH₃ | H | 5-OCH₃ | C₂H₅ | H | |
| NO₂ | H | H | C₂H₅ | Cl | |
| SO₂CH₃ | H | H | C₂H₅ | Br | |
| Cl | H | H | C₂H₅ | CH₃ | |
| CH₃ | H | H | C₂H₅ | C₂H₅ | |
| CO₂CH₃ | CH₃ | H | C₂H₅ | Cl | |
| CO₂CH₃ | H | 5-CF₃ | C₂H₅ | CH | |
| CO₂CH₃ | H | H | CH₂CH₂CH₃ | H | |
| NO₂ | CH₃ | H | CH₂CH₂CH₃ | H | |
| CO₂CH₃ | H | 5-CF₃ | CH₂CH₂CH₃ | H | |
| NO₂ | H | H | CH₂CH₂CH₃ | Cl | |
| SO₂N(CH₃)₂ | H | H | CH₂CH₂CH₃ | Br | |
| CO₂CH₃ | H | H | CH(CH₃)₂ | H | |
| CO₂CH₃ | H | H | CH(CH₃)₂ | H | |
| NO₂ | CH₃ | H | CH(CH₃)₂ | H | |
| CO₂CH₃ | H | 5-OCH₃ | CH(CH₃)₂ | Cl | |
| SO₂N(CH₃)₂ | H | H | CH(CH₃)₂ | Br | |
| CO₂CH₃ | H | H | N(CH₃)₂ | H | |
| CO₂CH₃ | CH₃ | H | N(CH₃)₂ | H | |
| NO₂ | H | H | N(CH₃)₂ | H | |
| NO₂ | H | 5-CH₃ | N(CH₃)₂ | H | |
| CO₂CH₃ | H | H | N(CH₃)₂ | Cl | |
| CO₂CH₃ | H | H | N(CH₃)₂ | Br | |
| CO₂CH₃ | H | H | H | H | |
| SCH₃ | H | H | H | H | |
| SCF₃ | H | H | H | H | |
| SOCH₃ | H | H | H | CH₃ | |
| SOCF₃ | H | H | H | CH₃ | |
| SO₂CH₃ | H | H | H | C₂H₅ | |
| OSO₂CH₃ | H | H | H | C₂H₅ | |
| OCH₂CH₂CH₃ | H | H | H | Br | |
| SO₂N(CH₃)₂ | H | H | H | Cl | |
| CH₂OCH₃ | CH₃ | H | H | H | |
| CH₂CH₂OCH₃ | CH₃ | H | H | H | |
| Cl | H | 5-Cl | H | H | |
| NO₂ | H | 5-Cl | H | H | |
| CF₃ | H | 5-NO₂ | H | CH₃ | |
| CH₃ | H | H | H | H | |

TABLE I-continued

| R₁ | R | R₂ | X | Y | m.p. (°C.) |
|---|---|---|---|---|---|
| CO₂CH₃ | H | H | Br | H | |
| CO₂CH₃ | CH₃ | H | Br | CH₃ | |
| CO₂CH₃ | H | 5-OCH₃ | Br | CH₃ | |
| NO₂ | H | H | Br | CH₃ | |
| SO₂N(CH₃)₂ | H | H | Br | Br | |
| CO₂CH₃ | H | H | Cl | H | |
| CO₂CH₃ | CH₃ | H | Cl | CH₃ | |
| CO₂CH₃ | H | H | Cl | C₂H₅ | |
| NO₂ | H | 5-CH₃ | Cl | Br | |
| SO₂N(CH₃)₂ | H | H | Cl | Cl | |
| CO₂CH₃ | H | H | OCH₃ | H | |
| CO₂CH₂CH₃ | H | H | OCH₃ | H | |
| CO₂CH₂CH₂CH₃ | H | H | OCH₃ | H | |
| CO₂CH(CH₃)₂ | H | H | OCH₃ | H | |
| CO₂CH₂CH₂CH₂CH₃ | H | H | OCH₃ | H | |
| CO₂CH₂CH=CH₂ | H | H | OCH₃ | H | |
| CO₂CH₂CH₂OCH₃ | H | H | OCH₃ | H | |
| CO₂CH₂CH₂Cl | H | H | OCH₃ | H | |
| SCH₃ | H | H | OCH₃ | H | |
| SCH₂CH₃ | H | H | OCH₃ | H | |
| SCH(CH₃)₂ | H | H | OCH₃ | H | |
| SCH₂CH=CH₂ | H | H | OCH₃ | H | |
| SCF₃ | H | H | OCH₃ | H | |
| SCF₂H | H | H | OCH₃ | H | |
| SOCH₃ | H | H | OCH₃ | H | |
| SOCH₂CH₃ | H | H | OCH₃ | H | |
| SOCH(CH₃)₂ | H | H | OCH₃ | H | |
| SOCH₂CH=CH₂ | H | H | OCH₃ | H | |
| SOCF₃ | H | H | OCH₃ | H | |
| SOCF₂H | H | H | OCH₃ | H | |
| SOCF₂CF₂H | H | H | OCH₃ | H | |
| SO₂CH₃ | H | H | OCH₃ | H | |
| SO₂CH₂CH₃ | H | H | OCH₃ | H | |
| SO₂CH(CH₃)₂ | H | H | OCH₃ | H | |
| SO₂CH₂CH=CH₂ | H | H | OCH₃ | H | |
| SO₂CF₃ | H | H | OCH₃ | H | |
| SO₂CF₂H | H | H | OCH₃ | H | |
| SO₂CF₂CF₂H | H | H | OCH₃ | H | |
| OSO₂CH₃ | H | H | OCH₃ | H | |
| OSO₂CH₂CH₃ | H | H | OCH₃ | H | |
| OSO₂CH(CH₃)₂ | H | H | OCH₃ | H | |
| OCH₃ | H | H | OCH₃ | H | |
| OCH₂CH₃ | H | H | OCH₃ | H | |
| OCH(CH₃)₂ | H | H | OCH₃ | H | |
| OCH₂CH₂CH₂CH₃ | H | H | OCH₃ | H | |
| OCH₂CH=CH₂ | H | H | OCH₃ | H | |
| OCH₂CH₂CH=CH₂ | H | H | OCH₃ | H | |
| OCH(CH₃)CH=CH₂ | H | H | OCH₃ | H | |
| SO₂N(CH₃)₂ | H | H | OCH₃ | H | |
| SO₂N(CH₃)CH(CH₃)₂ | H | H | OCH₃ | H | |
| SO₂N(OCH₃)CH₃ | H | H | OCH₃ | H | |
| CH₂OCH₃ | H | H | OCH₃ | H | |
| CH₂CH₂OCH₃ | H | H | OCH₃ | H | |
| F | H | H | OCH₃ | H | |
| Cl | H | H | OCH₃ | H | |
| Br | H | H | OCH₃ | H | |
| NO₂ | H | H | OCH₃ | H | |
| CF₃ | H | H | OCH₃ | H | |
| CH₃ | H | H | OCH₃ | H | |
| CH₂CH₃ | H | H | OCH₃ | H | |
| CH(CH₃)₂ | H | H | OCH₃ | H | |
| CH₂CH₂CH₂CH₃ | H | H | OCH₃ | H | |
| CO₂CH₃ | CH₃ | H | OCH₃ | H | |
| SCH₃ | CH₃ | H | OCH₃ | H | |
| SCF₃ | CH₃ | H | OCH₃ | H | |
| SOCH₃ | CH₃ | H | OCH₃ | H | |
| SOCF₃ | CH₃ | H | OCH₃ | H | |
| SO₂CH₃ | CH₃ | H | OCH₃ | H | |
| SO₂CF₃ | CH₃ | H | OCH₃ | H | |
| OSO₂CH₃ | CH₃ | H | OCH₃ | H | |

TABLE I-continued

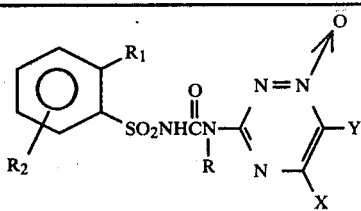

| $R_1$ | R | $R_2$ | X | Y | m.p. (°C.) |
|---|---|---|---|---|---|
| $OCH_3$ | $CH_3$ | H | $OCH_3$ | H | |
| $SO_2N(CH_3)_2$ | $CH_3$ | H | $OCH_3$ | H | |
| $SO_2N(OCH_3)CH_3$ | $CH_3$ | H | $OCH_3$ | H | |
| $CH_2OCH_3$ | $CH_3$ | H | $OCH_3$ | H | |
| $CH_2CH_2OCH_3$ | $CH_3$ | H | $OCH_3$ | H | |
| Cl | $CH_3$ | H | $OCH_3$ | H | |
| $NO_2$ | $CH_3$ | H | $OCH_3$ | H | |
| $CF_3$ | $CH_3$ | H | $OCH_3$ | H | |
| $CH_3$ | $CH_3$ | H | $OCH_3$ | H | |
| $NO_2$ | H | 5-$CF_3$ | $OCH_3$ | H | |
| $NO_2$ | H | 3-Cl | $OCH_3$ | H | |
| Cl | H | 6-$NO_2$ | $OCH_3$ | H | |
| $CF_3$ | H | 5-$NO_2$ | $OCH_3$ | H | |
| Cl | H | 5-Cl | $OCH_3$ | H | |
| $NO_2$ | H | 5-Cl | $OCH_3$ | H | |
| $SO_2N(CH_3)_2$ | H | 3-Cl | $OCH_3$ | H | |
| $CO_2CH_3$ | H | 5-$CH_3$ | $OCH_3$ | H | |
| Cl | H | 3-Br | $OCH_3$ | H | |
| Cl | H | 5-Br | $OCH_3$ | H | |
| $NO_2$ | H | 6-F | $OCH_3$ | H | |
| Cl | H | 6-F | $OCH_3$ | H | |
| Br | H | 3-F | $OCH_3$ | H | |
| $NO_2$ | $CH_3$ | 5-$NO_2$ | $OCH_3$ | H | |
| $CO_2CH_3$ | $CH_3$ | 3-$OCH_3$ | $OCH_3$ | H | |
| $CH_3$ | $CH_3$ | 3-$NO_2$ | $OCH_3$ | H | |
| $CO_2CH_3$ | H | H | $OCH_3$ | Cl | |
| $NO_2$ | H | H | $OCH_3$ | Cl | |
| Cl | H | H | $OCH_3$ | Cl | |
| $OCH_2CH_2CH_3$ | H | H | $OCH_3$ | Cl | |
| $SO_2N(CH_3)_2$ | H | H | $OCH_3$ | Cl | |
| $CO_2CH_3$ | $CH_3$ | H | $OCH_3$ | Cl | |
| $CO_2CH_3$ | H | 5-$CF_3$ | $OCH_3$ | Cl | |
| $NO_2$ | $CH_3$ | 5-Cl | $OCH_3$ | Cl | |
| $CO_2CH_3$ | H | H | $OCH_3$ | Br | |
| $NO_2$ | H | H | $OCH_3$ | Br | |
| Cl | H | H | $OCH_3$ | Br | |
| $CO_2CH_3$ | H | 5-$OCH_3$ | $OCH_3$ | Br | |
| $CO_2CH_3$ | $CH_3$ | H | $OCH_3$ | Br | |
| $CO_2CH_3$ | H | H | $OCH_3$ | $C_2H_5$ | |
| $NO_2$ | H | H | $OCH_3$ | $C_2H_5$ | |
| $SO_2N(CH_3)_2$ | H | 3-Cl | $OCH_3$ | $C_2H_5$ | |
| $OCH_2CH_2CH_3$ | H | H | $OCH_3$ | $C_2H_5$ | |
| $CO_2CH_3$ | $CH_3$ | H | $OCH_3$ | $C_2H_5$ | |
| $CO_2CH_3$ | H | H | $OC_2H_5$ | H | |
| $SO_2CH_3$ | H | H | $OC_2H_5$ | H | |
| $OSO_2CH_3$ | H | H | $OC_2H_5$ | H | |
| $OCH_2CH_2CH_3$ | H | H | $OC_2H_5$ | H | |
| $CH_2OCH_3$ | H | H | $OC_2H_5$ | H | |
| $CH_2CH_2OCH_3$ | H | H | $OC_5H_5$ | H | |
| Cl | H | H | $OC_2H_5$ | H | |
| $NO_2$ | H | H | $OC_2H_5$ | H | |
| $CF_3$ | H | H | $OC_2H_5$ | H | |
| $CO_2CH_3$ | $CH_3$ | H | $OC_2H_5$ | H | |
| $CO_2CH_3$ | H | 5-$OCH_3$ | $OC_2H_5$ | H | |
| $NO_2$ | H | H | $OC_2H_5$ | Cl | |
| $SO_2CH_3$ | H | H | $OC_2H_5$ | Br | |
| Cl | H | H | $OC_2H_5$ | $CH_3$ | |
| $CH_3$ | H | H | $OC_2H_5$ | $C_2H_5$ | |
| $CO_2CH_3$ | $CH_3$ | H | $OC_2H_5$ | Cl | |
| $CO_2CH_3$ | H | 5-$CF_3$ | $OC_2H_5$ | $CH_3$ | |
| $CO_2CH_3$ | H | H | $OCH_2CH_2CH_3$ | H | |
| $NO_2$ | $CH_3$ | H | $OCH_2CH_2CH_3$ | H | |
| $CO_2CH_3$ | H | 5-$CF_3$ | $OCH_2CH_2CH_3$ | H | |
| $NO_2$ | H | H | $OCH_2CH_2CH_3$ | Cl | |
| $SO_2N(CH_3)_2$ | H | H | $OCH_2CH_2CH_3$ | Br | |
| $CO_2CH_3$ | H | H | $OCH(CH_3)_2$ | H | |
| $CO_2CH_3$ | H | H | $OCH(CH_3)_2$ | H | |
| $NO_2$ | $CH_3$ | H | $OCH(CH_3)_2$ | H | |
| $CO_2CH_3$ | H | 5-$OCH_3$ | $OCH(CH_3)_2$ | Cl | |
| $SO_2N(CH_3)_2$ | H | H | $OCH(CH_3)_2$ | Br | |

TABLE I-continued

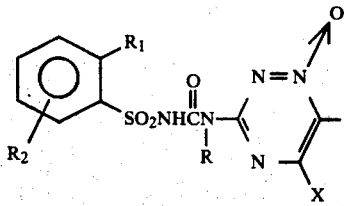

| R₁ | R | R₂ | X | Y | m.p. (°C.) |
|---|---|---|---|---|---|
| CO₂CH₃ | H | H | SCH₃ | H | |
| CO₂CH₂CH₃ | H | H | SCH₃ | H | |
| CO₂CH₂CH₂CH₃ | H | H | SCH₃ | H | |
| CO₂CH(CH₃)₂ | H | H | SCH₃ | H | |
| CO₂CH₂CH₂CH₂CH₃ | H | H | SCH₃ | H | |
| CO₂CH₂CH=CH₂ | H | H | SCH₃ | H | |
| CO₂CH₂CH₂OCH₃ | H | H | SCH₃ | H | |
| CO₂CH₂CH₂Cl | H | H | SCH₃ | H | |
| SCH₃ | H | H | SCH₃ | H | |
| SCH₂CH₃ | H | H | SCH₃ | H | |
| SCH(CH₃)₂ | H | H | SCH₃ | H | |
| SCH₂CH=CH₂ | H | H | SCH₃ | H | |
| SCF₃ | H | H | SCH₃ | H | |
| SCF₂H | H | H | SCH₃ | H | |
| SOCH₃ | H | H | SCH₃ | H | |
| SOCH₂CH₃ | H | H | SCH₃ | H | |
| SOCH(CH₃)₂ | H | H | SCH₃ | H | |
| SOCH₂CH=CH₂ | H | H | SCH₃ | H | |
| SOCF₃ | H | H | SCH₃ | H | |
| SOCF₂H | H | H | SCH₃ | H | |
| SOCF₂CF₂H | H | H | SCH₃ | H | |
| SO₂CH₃ | H | H | SCH₃ | H | |
| SO₂CH₂CH₃ | H | H | SCH₃ | H | |
| SO₂CH(CH₃)₂ | H | H | SCH₃ | H | |
| SO₂CH₂CH=CH₂ | H | H | SCH₃ | H | |
| SO₂CF₃ | H | H | SCH₃ | H | |
| SO₂CF₂H | H | H | SCH₃ | H | |
| SO₂CF₂CF₂H | H | H | SCH₃ | H | |
| OSO₂CH₃ | H | H | SCH₃ | H | |
| OSO₂CH₂CH₃ | H | H | SCH₃ | H | |
| OSO₂CH(CH₃)₂ | H | H | SCH₃ | H | |
| OCH₃ | H | H | SCH₃ | H | |
| OCH₂CH₃ | H | H | SCH₃ | H | |
| OCH(CH₃)₂ | H | H | SCH₃ | H | |
| OCH₂CH₂CH₂CH₃ | H | H | SCH₃ | H | |
| OCH₂CH=CH₂ | H | H | SCH₃ | H | |
| OCH₂CH₂CH=CH₂ | H | H | SCH₃ | H | |
| OCH(CH₃)CH=CH₂ | H | H | SCH₃ | H | |
| SO₂N(CH₃)₂ | H | H | SCH₃ | H | |
| SO₂N(CH₃)CH(CH₃)₂ | H | H | SCH₃ | H | |
| SO₂N(OCH₃)CH₃ | H | H | SCH₃ | H | |
| CH₂OCH₃ | H | H | SCH₃ | H | |
| CH₂CH₂OCH₃ | H | H | SCH₃ | H | |
| F | H | H | SCH₃ | H | |
| Cl | H | H | SCH₃ | H | |
| Br | H | H | SCH₃ | H | |
| NO₂ | H | H | SCH₃ | H | |
| CF₃ | H | H | SCH₃ | H | |
| CH₃ | H | H | SCH₃ | H | |
| CH₂CH₃ | H | H | SCH₃ | H | |
| CH(CH₃)₂ | H | H | SCH₃ | H | |
| CH₂CH₂CH₂CH₃ | H | H | SCH₃ | H | |
| CO₂CH₃ | CH₃ | H | SCH₃ | H | |
| SCH₃ | CH₃ | H | SCH₃ | H | |
| SCF₃ | CH₃ | H | SCH₃ | H | |
| SOCH₃ | CH₃ | H | SCH₃ | H | |
| SOCF₃ | CH₃ | H | SCH₃ | H | |
| SO₂CH₃ | CH₃ | H | SCH₃ | H | |
| SO₂CF₃ | CH₃ | H | SCH₃ | H | |
| OSO₂CH₃ | CH₃ | H | SCH₃ | H | |
| OCH₃ | CH₃ | H | SCH₃ | H | |
| SO₂N(CH₃)₂ | CH₃ | H | SCH₃ | H | |
| SO₂N(OCH₃)CH₃ | CH₃ | H | SCH₃ | H | |
| CH₂OCH₃ | CH₃ | H | SCH₃ | H | |
| CH₂CH₂OCH₃ | CH₃ | H | SCH₃ | H | |
| Cl | CH₃ | H | SCH₃ | H | |
| NO₂ | CH₃ | H | SCH₃ | H | |
| CF₃ | CH₃ | H | SCH₃ | H | |
| CH₃ | CH₃ | H | SCH₃ | H | |
| NO₂ | H | 5-CF₃ | SCH₃ | H | |

TABLE I-continued

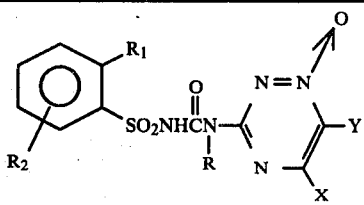

| $R_1$ | R | $R_2$ | X | Y | m.p. (°C.) |
|---|---|---|---|---|---|
| $NO_2$ | H | 3-Cl | $SCH_3$ | H | |
| Cl | H | 6-$NO_2$ | $SCH_3$ | H | |
| $CF_3$ | H | 5-$NO_2$ | $SCH_3$ | H | |
| Cl | H | 5-Cl | $SCH_3$ | H | |
| $NO_2$ | H | 5-Cl | $SCH_3$ | H | |
| $SO_2N(CH_3)_2$ | H | 3-Cl | $SCH_3$ | H | |
| $CO_2CH_3$ | H | 5-$CH_3$ | $SCH_3$ | H | |
| Cl | H | 3-Br | $SCH_3$ | H | |
| Cl | H | 5-Br | $SCH_3$ | H | |
| $NO_2$ | H | 6-F | $SCH_3$ | H | |
| Cl | H | 6-F | $SCH_3$ | H | |
| Br | H | 3-F | $SCH_3$ | H | |
| $NO_2$ | $CH_3$ | 5-$NO_2$ | $SCH_3$ | H | |
| $CO_2CH_3$ | $CH_3$ | 3-$OCH_3$ | $SCH_3$ | H | |
| $CH_3$ | $CH_3$ | 3-$NO_2$ | $SCH_3$ | H | |
| $CO_2CH_3$ | H | H | $SCH_3$ | Cl | |
| $NO_2$ | H | H | $SCH_3$ | Cl | |
| Cl | H | H | $SCH_3$ | Cl | |
| $OCH_2CH_2CH_3$ | H | H | $SCH_3$ | Cl | |
| $SO_2N(CH_3)_2$ | H | H | $SCH_3$ | Cl | |
| $CO_2CH_3$ | $CH_3$ | H | $SCH_3$ | Cl | |
| $CO_2CH_3$ | H | 5-$CF_3$ | $SCH_3$ | Cl | |
| $NO_2$ | $CH_3$ | 5-Cl | $SCH_3$ | Cl | |
| $CO_2CH_3$ | H | H | $SCH_3$ | Br | |
| $NO_2$ | H | H | $SCH_3$ | Br | |
| Cl | H | H | $SCH_3$ | Br | |
| $CO_2CH_3$ | H | 5-$OCH_3$ | $SCH_3$ | Br | |
| $CO_2CH_3$ | $CH_3$ | H | $SCH_3$ | Br | |
| $CO_2CH_3$ | H | H | $SCH_3$ | $C_2H_5$ | |
| $NO_2$ | H | H | $SCH_3$ | $C_2H_5$ | |
| $SO_2N(CH_3)_2$ | H | 3-Cl | $SCH_3$ | $C_2H_5$ | |
| $OCH_2CH_2CH_3$ | H | H | $SCH_3$ | $C_2H_5$ | |
| $CO_2CH_3$ | $CH_3$ | H | $SCH_3$ | $C_2H_5$ | |
| $CO_2CH_3$ | H | H | $SC_2H_5$ | H | |
| $SO_2CH_3$ | H | H | $SC_2H_5$ | H | |
| $OSO_2CH_3$ | H | H | $SC_2H_5$ | H | |
| $OCH_2CH_2CH_3$ | H | H | $SC_2H_5$ | H | |
| $CH_2OCH_3$ | H | H | $SC_2H_5$ | H | |
| $CH_2CH_2OCH_3$ | H | H | $SC_2H_5$ | H | |
| Cl | H | H | $SC_2H_5$ | H | |
| $NO_2$ | H | H | $SC_2H_5$ | H | |
| $CF_3$ | H | H | $SC_2H_5$ | H | |
| $CO_2CH_3$ | $CH_3$ | H | $SC_2H_5$ | H | |
| $CO_2CH_3$ | H | 5-$OCH_3$ | $SC_2H_5$ | H | |
| $NO_2$ | H | H | $SC_2H_5$ | Cl | |
| $SO_2CH_3$ | H | H | $SC_2H_5$ | Br | |
| Cl | H | H | $SC_2H_5$ | $CH_3$ | |
| $CH_3$ | H | H | $SC_2H_5$ | $C_2H_5$ | |
| $CO_2CH_3$ | $CH_3$ | H | $SC_2H_5$ | Cl | |
| $CO_2CH_3$ | H | 5-$CF_3$ | $SC_2H_5$ | $CH_3$ | |
| $CO_2CH_3$ | H | H | $SCH_2CH_2CH_3$ | H | |
| $NO_2$ | $CH_3$ | H | $SCH_2CH_2CH_3$ | H | |
| $CO_2CH_3$ | H | 5-$CF_3$ | $SCH_2CH_2CH_3$ | H | |
| $NO_2$ | H | H | $SCH_2CH_2CH_3$ | Cl | |
| $SO_2N(CH_3)_2$ | H | H | $SCH_2CH_2CH_3$ | Br | |
| $CO_2CH_3$ | H | H | $SCH(CH_3)_2$ | H | |
| $CO_2CH_3$ | H | H | $SCH(CH_3)_2$ | H | |
| $NO_2$ | $CH_3$ | H | $SCH(CH_3)_2$ | H | |
| $CO_2CH_3$ | H | 5-$OCH_3$ | $SCH(CH_3)_2$ | Cl | |
| $SO_2N(CH_3)_2$ | H | H | $SCH(CH_3)_2$ | Br | |

TABLE II

| $R_1$ | R | $R_2$ | X | Y | m.p. (°C.) |
|---|---|---|---|---|---|
| $CO_2CH_3$ | H | H | $CH_3$ | H | |
| $CO_2CH_2CH_3$ | H | H | $CH_3$ | H | |
| $CO_2CH(CH_3)_2$ | H | H | $CH_3$ | H | |
| $CO_2CH_2CH_2CH_2CH_3$ | H | H | $CH_3$ | H | |
| $CO_2CH_2CH=CH_2$ | H | H | $CH_3$ | H | |
| $SCH_3$ | H | H | $CH_3$ | H | |
| $SCH(CH_3)_2$ | H | H | $CH_3$ | H | |
| $SCF_3$ | H | H | $CH_3$ | H | |
| $SCF_2H$ | H | H | $CH_3$ | H | |
| $SOCH_3$ | H | H | $CH_3$ | H | |
| $SOCH(CH_3)_2$ | H | H | $CH_3$ | H | |
| $SOCF_3$ | H | H | $CH_3$ | H | |
| $SOCF_2CF_2H$ | H | H | $CH_3$ | H | |
| $SO_2CH_3$ | H | H | $CH_3$ | H | |
| $SO_2CH_2CH_3$ | H | H | $CH_3$ | H | |
| $SO_2CH_2CH_2CH_3$ | H | H | $CH_3$ | H | |
| $SO_2CH_2CH=CH_2$ | H | H | $CH_3$ | H | |
| $SO_2CF_3$ | H | H | $CH_3$ | H | |
| $OSO_2CH_3$ | H | H | $CH_3$ | H | |
| $OSO_2CH(CH_3)_2$ | H | H | $CH_3$ | H | |
| $OCH_3$ | H | H | $CH_3$ | H | |
| $OCH_2CH_3$ | H | H | $CH_3$ | H | |
| $OCH(CH_3)_2$ | H | H | $CH_3$ | H | |
| $OCH_2CH_2CH_2CH_3$ | H | H | $CH_3$ | H | |
| $OCH_2CH=CH_2$ | H | H | $CH_3$ | H | |
| $SO_2N(CH_3)_2$ | H | H | $CH_3$ | H | |
| $SO_2N(OCH_3)CH_3$ | H | H | $CH_3$ | H | |
| $CH_2OCH_3$ | H | H | $CH_3$ | H | |
| $CH_2CH_2OCH_3$ | H | H | $CH_3$ | H | |
| F | H | H | $CH_3$ | H | |
| Cl | H | H | $CH_3$ | H | |
| Br | H | H | $CH_3$ | H | |
| $NO_2$ | H | H | $CH_3$ | H | |
| $CF_3$ | H | H | $CH_3$ | H | |
| $CH_3$ | H | H | $CH_3$ | H | |
| $CO_2CH_3$ | $CH_3$ | H | $CH_3$ | H | |
| $NO_2$ | $CH_3$ | H | $CH_3$ | H | |
| Cl | $CH_3$ | H | $CH_3$ | H | |
| $OCH_2CH_2CH_3$ | $CH_3$ | H | $CH_3$ | H | |
| $CH_3$ | $CH_3$ | H | $CH_3$ | H | |
| $NO_2$ | H | $5-CF_3$ | $CH_3$ | H | |
| $NO_2$ | H | 3-Cl | $CH_3$ | H | |
| Cl | H | $6-NO_2$ | $CH_3$ | H | |
| $CF_3$ | H | $5-NO_2$ | $CH_3$ | H | |
| $CO_2CH_3$ | H | $5-CH_3$ | $CH_3$ | H | |
| $NO_2$ | $CH_3$ | $5-NO_2$ | $CH_3$ | H | |
| $CO_2CH_3$ | H | H | $CH_3$ | $C_2H_5$ | |
| $NO_2$ | H | H | $CH_3$ | $C_2H_5$ | |
| $SO_2N(CH_3)_2$ | H | H | $CH_3$ | $C_2H_5$ | |
| $CO_2CH_3$ | H | H | $C_2H_5$ | H | |
| $NO_2$ | H | H | $C_2H_5$ | H | |
| $SO_2CH_3$ | H | H | $C_2H_5$ | H | |
| $OSO_2CH_3$ | H | H | $C_2H_5$ | H | |
| Cl | H | H | $C_2H_5$ | H | |
| $OCH_3$ | H | H | $C_2H_5$ | $CH_3$ | |
| $NO_2$ | H | H | $C_2H_5$ | $CH_3$ | |
| Cl | H | H | $C_2H_5$ | $CH_3$ | |
| $SO_2CH_3$ | H | H | $C_2H_5$ | $C_2H_5$ | |
| $SO_2N(CH_3)_2$ | H | H | $C_2H_5$ | $C_2H_5$ | |
| $CO_2CH_3$ | $CH_3$ | H | $C_2H_5$ | $C_2H_5$ | |
| $CO_2CH_3$ | H | $5-OCH_3$ | $C_2H_5$ | $C_2H_5$ | |
| $CO_2CH_3$ | H | H | $CH_2CH_2CH_3$ | H | |
| $NO_2$ | H | H | $CH_2CH_2CH_3$ | H | |
| $SO_2CF_3$ | H | H | $CH_2CH_2CH_3$ | $CH_3$ | |
| $CO_2CH_3$ | H | H | $CH(CH_3)_2$ | H | |
| $NO_2$ | $CH_3$ | H | $CH(CH_3)_2$ | H | |
| $CO_2CH_3$ | H | $5-CH_3$ | $CH(CH_3)_2$ | $CH_3$ | |
| $CO_2CH_3$ | H | H | $N(CH_3)_2$ | H | |
| Cl | H | H | $N(CH_3)_2$ | H | |
| $OCH_3$ | H | H | $N(CH_3)_2$ | H | |

TABLE II-continued

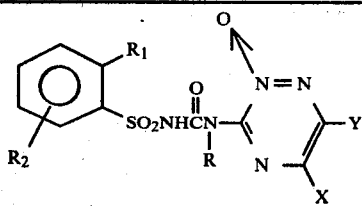

| $R_1$ | R | $R_2$ | X | Y | m.p. (°C.) |
|---|---|---|---|---|---|
| $CO_2CH_3$ | $CH_3$ | H | $N(CH_3)_2$ | $CH_3$ | |
| $CO_2CH_3$ | H | 5-$OCH_3$ | $N(CH_3)_2$ | $CH_3$ | |
| $SO_2N(CH_3)_2$ | H | H | H | H | |
| $CO_2CH_3$ | $CH_3$ | H | H | H | |
| $NO_2$ | H | 5-$NO_2$ | H | H | |
| Cl | H | H | H | $CH_3$ | |
| $OSO_2CH_3$ | H | H | H | $CH_3$ | |
| $CO_2CH_3$ | H | H | H | $C_2H_5$ | |
| $CO_2CH_3$ | H | H | Br | H | |
| $CO_2CH_3$ | $CH_3$ | H | Br | H | |
| $NO_2$ | H | H | Br | H | |
| $CO_2CH_3$ | H | 5-$OCH_3$ | Br | $CH_3$ | |
| $SO_2N(CH_3)_2$ | H | H | Br | $C_2H_5$ | |
| Cl | H | H | Cl | H | |
| $CO_2CH_3$ | $CH_3$ | H | Cl | H | |
| $SCF_3$ | H | H | Cl | H | |
| $CO_2CH_3$ | H | H | Cl | $CH_3$ | |
| $CH_2OCH_3$ | H | H | Cl | $C_2H_5$ | |
| $CO_2CH_3$ | H | H | H | Br | |
| $NO_2$ | H | H | $CH_3$ | Br | |
| Cl | H | H | $OCH_3$ | Br | |
| $CO_2CH_3$ | H | H | H | Cl | |
| $SO_2CF_3$ | H | H | $CH_3$ | Cl | |
| Br | H | H | $OCH_3$ | Cl | |
| $CO_2CH_3$ | H | H | $OCH_3$ | H | |
| $CO_2CH_2CH_3$ | H | H | $OCH_3$ | H | |
| $CO_2CH(CH_3)_2$ | H | H | $OCH_3$ | H | |
| $CO_2CH_2CH_2CH_2CH_3$ | H | H | $OCH_3$ | H | |
| $CO_2CH_2CH_2=CH_2$ | H | H | $OCH_3$ | H | |
| $SCH_3$ | H | H | $OCH_3$ | H | |
| $SCH(CH_3)_2$ | H | H | $OCH_3$ | H | |
| $SCF_3$ | H | H | $OCH_3$ | H | |
| $SCF_2H$ | H | H | $OCH_3$ | H | |
| $SOCH_3$ | H | H | $OCH_3$ | H | |
| $SOCH(CH_3)_2$ | H | H | $OCH_3$ | H | |
| $SOCF_3$ | H | H | $OCH_3$ | H | |
| $SOCF_2CF_2H$ | H | H | $OCH_3$ | H | |
| $SO_2CH_3$ | H | H | $OCH_3$ | H | |
| $SO_2CH_2CH_3$ | H | H | $OCH_3$ | H | |
| $SO_2CH_2CH_2CH_3$ | H | H | $OCH_3$ | H | |
| $SO_2CH_2CH=CH_2$ | H | H | $OCH_3$ | H | |
| $SO_2CF_3$ | H | H | $OCH_3$ | H | |
| $OSO_2CH_3$ | H | H | $OCH_3$ | H | |
| $OSO_2CH(CH_3)_2$ | H | H | $OCH_3$ | H | |
| $OCH_3$ | H | H | $OCH_3$ | H | |
| $OCH_2CH_3$ | H | H | $OCH_3$ | H | |
| $OCH(CH_3)_2$ | H | H | $OCH_3$ | H | |
| $OCH_2CH_2CH_2CH_3$ | H | H | $OCH_3$ | H | |
| $OCH_2CH=CH_2$ | H | H | $OCH_3$ | H | |
| $SO_2N(CH_3)_2$ | H | H | $OCH_3$ | H | |
| $SO_2N(OCH_3)CH_3$ | H | H | $OCH_3$ | H | |
| $CH_2OCH_3$ | H | H | $OCH_3$ | H | |
| $CH_2CH_2OCH_3$ | H | H | $OCH_3$ | H | |
| F | H | H | $OCH_3$ | H | |
| Cl | H | H | $OCH_3$ | H | |
| Br | H | H | $OCH_3$ | H | |
| $NO_2$ | H | H | $OCH_3$ | H | |
| $CF_3$ | H | H | $OCH_3$ | H | |
| $CH_3$ | H | H | $OCH_3$ | H | |
| $CO_2CH_3$ | $CH_3$ | H | $OCH_3$ | H | |
| $NO_2$ | $CH_3$ | H | $OCH_3$ | H | |
| Cl | $CH_3$ | H | $OCH_3$ | H | |
| $OCH_2CH_2CH_3$ | $CH_3$ | H | $OCH_3$ | H | |
| $CH_3$ | $CH_3$ | H | $OCH_3$ | H | |
| $NO_2$ | H | 5-$CF_3$ | $OCH_3$ | H | |
| $NO_2$ | H | 3-Cl | $OCH_3$ | H | |
| Cl | H | 6-$NO_2$ | $OCH_3$ | H | |
| $CF_3$ | H | 5-$NO_2$ | $OCH_3$ | H | |
| $CO_2CH_3$ | H | 5-$CH_3$ | $OCH_3$ | H | |
| $NO_2$ | $CH_3$ | 5-$NO_2$ | $OCH_3$ | H | |

TABLE II-continued

| R₁ | R | R₂ | X | Y | m.p. (°C.) |
|---|---|---|---|---|---|
| CO₂CH₃ | H | H | OCH₃ | C₂H₅ | |
| NO₂ | H | H | OCH₃ | C₂H₅ | |
| SO₂N(CH₃)₂ | H | H | OCH₃ | C₂H₅ | |
| CO₂CH₃ | H | H | OC₂H₅ | H | |
| NO₂ | H | H | OC₂H₅ | H | |
| SO₂CH₃ | H | H | OC₂H₅ | H | |
| OSO₂CH₃ | H | H | OC₂H₅ | H | |
| Cl | H | H | OC₂H₅ | H | |
| OCH₃ | H | H | OC₂H₅ | CH₃ | |
| NO₂ | H | H | OC₂H₅ | CH₃ | |
| Cl | H | H | OC₂H₅ | CH₃ | |
| SO₂CH₃ | H | H | OC₂H₅ | C₂H₅ | |
| SO₂N(CH₃)₂ | H | H | OC₂H₅ | C₂H₅ | |
| CO₂CH₃ | CH₃ | H | OC₂H₅ | C₂H₅ | |
| CO₂CH₃ | H | 5-OCH₃ | OC₂H₅ | CH₃ | |
| CO₂CH₃ | H | H | OCH₂CH₂CH₃ | H | |
| NO₂ | H | H | OCH₂CH₂CH₃ | H | |
| SO₂CF₃ | H | H | OCH₂CH₂CH₃ | CH₃ | |
| CO₂CH₃ | H | H | OCH(CH₃)₂ | H | |
| NO₂ | CH₃ | H | OCH(CH₃)₂ | H | |
| CO₂CH₃ | H | 5-CH₃ | OCH(CH₃)₂ | CH₃ | |
| CO₂CH₃ | H | H | SCH₃ | H | |
| CO₂CH₂CH₃ | H | H | SCH₃ | H | |
| CO₂CH(CH₃)₂ | H | H | SCH₃ | H | |
| CO₂CH₂CH₂CH₂CH₃ | H | H | SCH₃ | H | |
| CO₂CH₂CH₂=CH₂ | H | H | SCH₃ | H | |
| SCH₃ | H | H | SCH₃ | H | |
| SCH(CH₃)₂ | H | H | SCH₃ | H | |
| SCF₃ | H | H | SCH₃ | H | |
| SCF₂H | H | H | SCH₃ | H | |
| SOCH₃ | H | H | SCH₃ | H | |
| SOCH(CH₃)₂ | H | H | SCH₃ | H | |
| SOCF₃ | H | H | SCH₃ | H | |
| SOCF₂CF₂H | H | H | SCH₃ | H | |
| SO₂CH₃ | H | H | SCH₃ | H | |
| SO₂CH₂CH₃ | H | H | SCH₃ | H | |
| SO₂CH₂CH₂CH₃ | H | H | SCH₃ | H | |
| SO₂CH₂CH=CH₂ | H | H | SCH₃ | H | |
| SO₂CF₃ | H | H | SCH₃ | H | |
| OSO₂CH₃ | H | H | SCH₃ | H | |
| OSO₂CH(CH₃)₂ | H | H | SCH₃ | H | |
| OCH₃ | H | H | SCH₃ | H | |
| OCH₂CH₃ | H | H | SCH₃ | H | |
| OCH(CH₃)₂ | H | H | SCH₃ | H | |
| OCH₂CH₂CH₂CH₃ | H | H | SCH₃ | H | |
| OCH₂CH=CH₂ | H | H | SCH₃ | H | |
| SO₂N(CH₃)₂ | H | H | SCH₃ | H | |
| SO₂N(OCH₃)CH₃ | H | H | SCH₃ | H | |
| CH₂OCH₃ | H | H | SCH₃ | H | |
| CH₂CH₂OCH₃ | H | H | SCH₃ | H | |
| F | H | H | SCH₃ | H | |
| Cl | H | H | SCH₃ | H | |
| Br | H | H | SCH₃ | H | |
| NO₂ | H | H | SCH₃ | H | |
| CF₃ | H | H | SCH₃ | H | |
| CH₃ | H | H | SCH₃ | H | |
| CO₂CH₃ | CH₃ | H | SCH₃ | H | |
| NO₂ | CH₃ | H | SCH₃ | H | |
| Cl | CH₃ | H | SCH₃ | H | |
| OCH₂CH₂CH₃ | CH₃ | H | SCH₃ | H | |
| CH₃ | CH₃ | H | SCH₃ | H | |
| NO₂ | H | 5-CF₃ | SCH₃ | H | |
| NO₂ | H | 3-Cl | SCH₃ | H | |
| Cl | H | 6-NO₂ | SCH₃ | H | |
| CF₃ | H | 5-NO₂ | SCH₃ | H | |
| CO₂CH₃ | H | 5-CH₃ | SCH₃ | H | |
| NO₂ | CH₃ | 5-NO₂ | SCH₃ | H | |
| CO₂CH₃ | H | H | SCH₃ | C₂H₅ | |
| NO₂ | H | H | SCH₃ | C₂H₅ | |
| SO₂N(CH₃)₂ | H | H | SCH₃ | C₂H₅ | |

TABLE II-continued

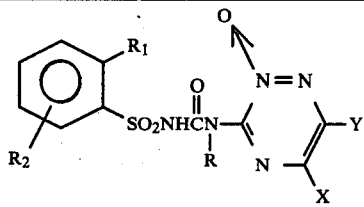

| R$_1$ | R | R$_2$ | X | Y | m.p. (°C.) |
|---|---|---|---|---|---|
| CO$_2$CH$_3$ | H | H | SC$_2$H$_5$ | H | |
| NO$_2$ | H | H | SC$_2$H$_5$ | H | |
| SO$_2$CH$_3$ | H | H | SC$_2$H$_5$ | H | |
| OSO$_2$CH$_3$ | H | H | SC$_2$H$_5$ | H | |
| Cl | H | H | SC$_2$H$_5$ | H | |
| OCH$_3$ | H | H | SC$_2$H$_5$ | CH$_3$ | |
| NO$_2$ | H | H | SC$_2$H$_5$ | CH$_3$ | |
| Cl | H | H | SC$_2$H$_5$ | CH$_3$ | |
| SO$_2$CH$_3$ | H | H | SC$_2$H$_5$ | C$_2$H$_5$ | |
| SO$_2$N(CH$_3$)$_2$ | H | H | SC$_2$H$_5$ | C$_2$H$_5$ | |
| CO$_2$CH$_3$ | CH$_3$ | H | SC$_2$H$_5$ | C$_2$H$_5$ | |
| CO$_2$CH$_3$ | H | 5-OCH$_3$ | SC$_2$H$_5$ | CH$_3$ | |
| CO$_2$CH$_3$ | H | H | SCH$_2$CH$_2$CH$_3$ | H | |
| NO$_2$ | H | H | SCH$_2$CH$_2$CH$_3$ | H | |
| SO$_2$CF$_3$ | H | H | SCH$_2$CH$_2$CH$_3$ | CH$_3$ | |
| CO$_2$CH$_3$ | H | H | SCH(CH$_3$)$_2$ | H | |
| NO$_2$ | CH$_3$ | H | SCH(CH$_3$)$_2$ | H | |
| CO$_2$CH$_3$ | H | 5-CH$_3$ | SCH(CH$_3$)$_2$ | CH$_3$ | |

TABLE III

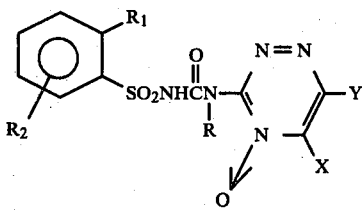

| R$_1$ | R | R$_2$ | X | Y | m.p. (°C.) |
|---|---|---|---|---|---|
| CO$_2$CH$_3$ | H | H | CH$_3$ | H | |
| CO$_2$CH$_2$CH$_3$ | H | H | CH$_3$ | H | |
| CO$_2$CH(CH$_3$)$_2$ | H | H | CH$_3$ | H | |
| CO$_2$CH$_2$CH$_2$CH$_2$CH$_3$ | H | H | CH$_3$ | H | |
| CO$_2$CH$_2$CH$_2$CH=CH$_2$ | H | H | CH$_3$ | H | |
| SCH$_3$ | H | H | CH$_3$ | H | |
| SCH(CH$_3$)$_2$ | H | H | CH$_3$ | H | |
| SCF$_3$ | H | H | CH$_3$ | H | |
| SCF$_2$H | H | H | CH$_3$ | H | |
| SOCH$_3$ | H | H | CH$_3$ | H | |
| SOCH(CH$_3$)$_2$ | H | H | CH$_3$ | H | |
| SOCF$_3$ | H | H | CH$_3$ | H | |
| SOCF$_2$CF$_2$H | H | H | CH$_3$ | H | |
| SO$_2$CH$_3$ | H | H | CH$_3$ | H | |
| SO$_2$CH$_2$CH$_3$ | H | H | CH$_3$ | H | |
| SO$_2$CH$_2$CH$_2$CH$_3$ | H | H | CH$_3$ | H | |
| SO$_2$CH$_2$CH=CH$_2$ | H | H | CH$_3$ | H | |
| SO$_2$CF$_3$ | H | H | CH$_3$ | H | |
| OSO$_2$CH$_3$ | H | H | CH$_3$ | H | |
| OSO$_2$CH(CH$_3$)$_2$ | H | H | CH$_3$ | H | |
| OCH$_3$ | H | H | CH$_3$ | H | |
| OCH$_2$CH$_3$ | H | H | CH$_3$ | H | |
| OCH(CH$_3$)$_2$ | H | H | CH$_3$ | H | |
| OCH$_2$CH$_2$CH$_3$ | H | H | CH$_3$ | H | |
| OCH$_2$CH=CH$_2$ | H | H | CH$_3$ | H | |
| SO$_2$N(CH$_3$)$_2$ | H | H | CH$_3$ | H | |
| SO$_2$N(OCH$_3$)CH$_3$ | H | H | CH$_3$ | H | |
| CH$_2$OCH$_3$ | H | H | CH$_3$ | H | |
| CH$_2$CH$_2$OCH$_3$ | H | H | CH$_3$ | H | |
| F | H | H | CH$_3$ | H | |
| Cl | H | H | CH$_3$ | H | |
| Br | H | H | CH$_3$ | H | |
| NO$_2$ | H | H | CH$_3$ | H | |
| CF$_3$ | H | H | CH$_3$ | H | |
| CH$_3$ | H | H | CH$_3$ | H | |
| CO$_2$CH$_3$ | CH$_3$ | H | CH$_3$ | H | |

TABLE III-continued

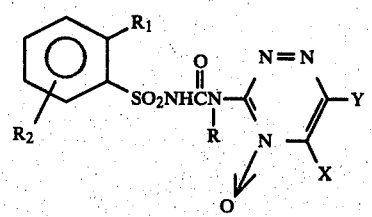

| $R_1$ | R | $R_2$ | X | Y | m.p. (°C.) |
|---|---|---|---|---|---|
| $NO_2$ | $CH_3$ | H | $CH_3$ | H | |
| Cl | $CH_3$ | H | $CH_3$ | H | |
| $OCH_2CH_2CH_3$ | $CH_3$ | H | $CH_3$ | H | |
| $CH_3$ | $CH_3$ | H | $CH_3$ | H | |
| $NO_2$ | H | 5-$CF_3$ | $CH_3$ | H | |
| $NO_2$ | H | 3-Cl | $CH_3$ | H | |
| Cl | H | 6-$NO_2$ | $CH_3$ | H | |
| $CF_3$ | H | 5-$NO_2$ | $CH_3$ | H | |
| $CO_2CH_3$ | H | 5-$CH_3$ | $CH_3$ | H | |
| $NO_2$ | $CH_3$ | 5-$NO_2$ | $CH_3$ | H | |
| $CO_2CH_3$ | H | H | $CH_3$ | $C_2H_5$ | |
| $NO_2$ | H | H | $CH_3$ | $C_2H_5$ | |
| $SO_2N(CH_3)_2$ | H | H | $CH_3$ | $C_2H_5$ | |
| $CO_2CH_3$ | H | H | $C_2H_5$ | H | |
| $NO_2$ | H | H | $C_2H_5$ | H | |
| $SO_2CH_3$ | H | H | $C_2H_5$ | H | |
| $OSO_2CH_3$ | H | H | $C_2H_5$ | H | |
| Cl | H | H | $C_2H_5$ | H | |
| $OCH_3$ | H | H | $C_2H_5$ | $CH_3$ | |
| $NO_2$ | H | H | $C_2H_5$ | $CH_3$ | |
| Cl | H | H | $C_2H_5$ | $CH_3$ | |
| $SO_2CH_3$ | H | H | $C_2H_5$ | $C_2H_5$ | |
| $SO_2N(CH_3)_2$ | H | H | $C_2H_5$ | $C_2H_5$ | |
| $CO_2CH_3$ | $CH_3$ | H | $C_2H_5$ | $C_2H_5$ | |
| $CO_2CH_3$ | H | 5-$OCH_3$ | $C_2H_5$ | $C_2H_5$ | |
| $CO_2CH_3$ | H | H | $CH_2CH_2CH_3$ | H | |
| $NO_2$ | H | H | $CH_2CH_2CH_3$ | H | |
| $SO_2CF_3$ | H | H | $CH_2CH_2CH_3$ | $CH_3$ | |
| $CO_2CH_3$ | H | H | $CH(CH_3)_2$ | H | |
| $NO_2$ | $CH_3$ | H | $CH(CH_3)_2$ | H | |
| $CO_2CH_3$ | H | 5-$CH_3$ | $CH(CH_3)_2$ | $CH_3$ | |
| $CO_2CH_3$ | H | H | $N(CH_3)_2$ | H | |
| Cl | H | H | $N(CH_3)_2$ | H | |
| $OCH_3$ | H | H | $N(CH_3)_2$ | H | |
| $CO_2CH_3$ | $CH_3$ | H | $N(CH_3)_2$ | $CH_3$ | |
| $CO_2CH_3$ | H | 5-$OCH_3$ | $N(CH_3)_2$ | $CH_3$ | |
| $SO_2N(CH_3)_2$ | H | H | H | H | |
| $CO_2CH_3$ | $CH_3$ | H | H | H | |
| $NO_2$ | H | 5-$NO_2$ | H | H | |
| Cl | H | H | H | $CH_3$ | |
| $OSO_2CH_3$ | H | H | H | $CH_3$ | |
| $CO_2CH_3$ | H | H | H | $C_2H_5$ | |
| $CO_2CH_3$ | H | H | Br | H | |
| $CO_2CH_3$ | $CH_3$ | H | Br | H | |
| $NO_2$ | H | H | Br | H | |
| $CO_2CH_3$ | H | 5-$OCH_3$ | Br | $CH_3$ | |
| $SO_2N(CH_3)_2$ | H | H | Br | $C_2H_5$ | |
| Cl | H | H | Cl | H | |
| $CO_2CH_3$ | $CH_3$ | H | Cl | H | |
| $SCF_3$ | H | H | Cl | H | |
| $CO_2CH_3$ | H | H | Cl | $CH_3$ | |
| $CH_2OCH_3$ | H | H | Cl | $C_2H_5$ | |
| $CO_2CH_3$ | H | H | H | Br | |
| $NO_2$ | H | H | $CH_3$ | Br | |
| Cl | H | H | $OCH_3$ | Br | |
| $CO_2CH_3$ | H | H | H | Cl | |
| $SO_2CF_3$ | H | H | $CH_3$ | Cl | |
| Br | H | H | $OCH_3$ | Cl | |
| $CO_2CH_3$ | H | H | $OCH_3$ | H | |
| $CO_2CH_2CH_3$ | H | H | $OCH_3$ | H | |
| $CO_2CH(CH_3)_2$ | H | H | $OCH_3$ | H | |
| $CO_2CH_2CH_2CH_2CH_3$ | H | H | $OCH_3$ | H | |
| $CO_2CH_2CH=CH_2$ | H | H | $OCH_3$ | H | |
| $SCH_3$ | H | H | $OCH_3$ | H | |
| $SCH(CH_3)_2$ | H | H | $OCH_3$ | H | |
| $SCF_3$ | H | H | $OCH_3$ | H | |
| $SCF_2H$ | H | H | $OCH_3$ | H | |
| $SOCH_3$ | H | H | $OCH_3$ | H | |
| $SOCH(CH_3)_2$ | H | H | $OCH_3$ | H | |
| $SOCF_3$ | H | H | $OCH_3$ | H | |

TABLE III-continued

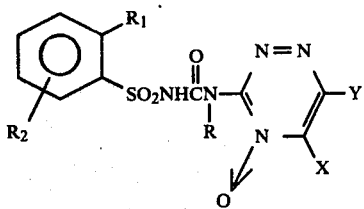

| R₁ | R | R₂ | X | Y | m.p. (°C.) |
|---|---|---|---|---|---|
| SOCF₂CF₂H | H | H | OCH₃ | H | |
| SO₂CH₃ | H | H | OCH₃ | H | |
| SO₂CH₂CH₃ | H | H | OCH₃ | H | |
| SO₂CH₂CH₂CH₃ | H | H | OCH₃ | H | |
| SO₂CH₂CH=CH₂ | H | H | OCH₃ | H | |
| SO₂CF₃ | H | H | OCH₃ | H | |
| OSO₂CH₃ | H | H | OCH₃ | H | |
| OSO₂CH(CH₃)₂ | H | H | OCH₃ | H | |
| OCH₃ | H | H | OCH₃ | H | |
| OCH₂CH₃ | H | H | OCH₃ | H | |
| OCH(CH₃)₂ | H | H | OCH₃ | H | |
| OCH₂CH₂CH₂CH₃ | H | H | OCH₃ | H | |
| OCH₂CH=CH₂ | H | H | OCH₃ | H | |
| SO₂N(CH₃)₂ | H | H | OCH₃ | H | |
| SO₂N(OCH₃)CH₃ | H | H | OCH₃ | H | |
| CH₂OCH₃ | H | H | OCH₃ | H | |
| CH₂CH₂OCH₃ | H | H | OCH₃ | H | |
| F | H | H | OCH₃ | H | |
| Cl | H | H | OCH₃ | H | |
| Br | H | H | OCH₃ | H | |
| NO₂ | H | H | OCH₃ | H | |
| CF₃ | H | H | OCH₃ | H | |
| CH₃ | H | H | OCH₃ | H | |
| CO₂CH₃ | CH₃ | H | OCH₃ | H | |
| NO₂ | CH₃ | H | OCH₃ | H | |
| Cl | CH₃ | H | OCH₃ | H | |
| OCH₂CH₂CH₃ | CH₃ | H | OCH₃ | H | |
| CH₃ | CH₃ | H | OCH₃ | H | |
| NO₂ | H | 5-CF₃ | OCH₃ | H | |
| NO₂ | H | 3-Cl | OCH₃ | H | |
| Cl | H | 6-NO₂ | OCH₃ | H | |
| CF₃ | H | 5-NO₂ | OCH₃ | H | |
| CO₂CH₃ | H | 5-CH₃ | OCH₃ | H | |
| NO₂ | CH₃ | 5-NO₂ | OCH₃ | H | |
| CO₂CH₃ | H | H | OCH₃ | C₂H₅ | |
| NO₂ | H | H | OCH₃ | C₂H₅ | |
| SO₂N(CH₃)₂ | H | H | OCH₃ | C₂H₅ | |
| CO₂CH₃ | H | H | OC₂H₅ | H | |
| NO₂ | H | H | OC₂H₅ | H | |
| SO₂CH₃ | H | H | OC₂H₅ | H | |
| OSO₂CH₃ | H | H | OC₂H₅ | H | |
| Cl | H | H | OC₂H₅ | H | |
| OCH₃ | H | H | OC₂H₅ | CH₃ | |
| NO₂ | H | H | OC₂H₅ | CH₃ | |
| Cl | H | H | OC₂H₅ | CH₃ | |
| SO₂CH₃ | H | H | OC₂H₅ | C₂H₅ | |
| SO₂N(CH₃)₂ | H | H | OC₂H₅ | C₂H₅ | |
| CO₂CH₃ | CH₃ | H | OC₂H₅ | C₂H₅ | |
| CO₂CH₃ | H | 5-OCH₃ | OC₂H₅ | CH₃ | |
| CO₂CH₃ | H | H | OCH₂CH₂CH₃ | H | |
| NO₂ | H | H | OCH₂CH₂CH₃ | H | |
| SO₂CF₃ | H | H | OCH₂CH₂CH₃ | CH₃ | |
| CO₂CH₃ | H | H | OCH(CH₃)₂ | H | |
| NO₂ | CH₃ | H | OCH(CH₃)₂ | H | |
| CO₂CH₃ | H | 5-CH₃ | OCH(CH₃)₂ | CH₃ | |
| CO₂CH₃ | H | H | SCH₃ | H | |
| CO₂CH₂CH₃ | H | H | SCH₃ | H | |
| CO₂CH(CH₃)₂ | H | H | SCH₃ | H | |
| CO₂CH₂CH₂CH₂CH₃ | H | H | SCH₃ | H | |
| CO₂CH₂CH=CH₂ | H | H | SCH₃ | H | |
| SCH₃ | H | H | SCH₃ | H | |
| SCH(CH₃)₂ | H | H | SCH₃ | H | |
| SCF₃ | H | H | SCH₃ | H | |
| SCF₂H | H | H | SCH₃ | H | |
| SOCH₃ | H | H | SCH₃ | H | |
| SOCH(CH₃)₂ | H | H | SCH₃ | H | |
| SOCF₃ | H | H | SCH₃ | H | |
| SOCF₂CF₂H | H | H | SCH₃ | H | |
| SO₂CH₃ | H | H | SCH₃ | H | |
| SO₂CH₂CH₃ | H | H | SCH₃ | H | |

TABLE III-continued

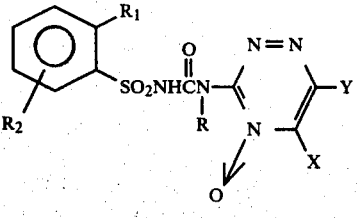

| R₁ | R | R₂ | X | Y | m.p. (°C.) |
|---|---|---|---|---|---|
| SO₂CH₂CH₂CH₃ | H | H | SCH₃ | H | |
| SO₂CH₂CH=CH₂ | H | H | SCH₃ | H | |
| SO₂CF₃ | H | H | SCH₃ | H | |
| OSO₂CH₃ | H | H | SCH₃ | H | |
| OSO₂CH(CH₃)₂ | H | H | SCH₃ | H | |
| OCH₃ | H | H | SCH₃ | H | |
| OCH₂CH₃ | H | H | SCH₃ | H | |
| OCH(CH₃)₂ | H | H | SCH₃ | H | |
| OCH₂CH₂CH₂CH₃ | H | H | SCH₃ | H | |
| OCH₂CH=CH₂ | H | H | SCH₃ | H | |
| SO₂N(CH₃)₂ | H | H | SCH₃ | H | |
| SO₂N(OCH₃)CH₃ | H | H | SCH₃ | H | |
| CH₂OCH₃ | H | H | SCH₃ | H | |
| CH₂CH₂OCH₃ | H | H | SCH₃ | H | |
| F | H | H | SCH₃ | H | |
| Cl | H | H | SCH₃ | H | |
| Br | H | H | SCH₃ | H | |
| NO₂ | H | H | SCH₃ | H | |
| CF₃ | H | H | SCH₃ | H | |
| CH₃ | H | H | SCH₃ | H | |
| CO₂CH₃ | CH₃ | H | SCH₃ | H | |
| NO₂ | CH₃ | H | SCH₃ | H | |
| Cl | CH₃ | H | SCH₃ | H | |
| OCH₂CH₂CH₃ | CH₃ | H | SCH₃ | H | |
| CH₃ | CH₃ | H | SCH₃ | H | |
| NO₂ | H | 5-CF₃ | SCH₃ | H | |
| NO₂ | H | 3-Cl | SCH₃ | H | |
| Cl | H | 6-NO₂ | SCH₃ | H | |
| CF₃ | H | 5-NO₂ | SCH₃ | H | |
| CO₂CH₃ | H | 5-CH₃ | SCH₃ | H | |
| NO₂ | CH₃ | 5-NO₂ | SCH₃ | H | |
| CO₂CH₃ | H | H | SCH₃ | C₂H₅ | |
| NO₂ | H | H | SCH₃ | C₂H₅ | |
| SO₂N(CH₃)₂ | H | H | SCH₃ | C₂H₅ | |
| CO₂CH₃ | H | H | SC₂H₅ | H | |
| NO₂ | H | H | SC₂H₅ | H | |
| SO₂CH₃ | H | H | SC₂H₅ | H | |
| OSO₂CH₃ | H | H | SC₂H₅ | H | |
| Cl | H | H | SC₂H₅ | H | |
| OCH₃ | H | H | SC₂H₅ | CH₃ | |
| NO₂ | H | H | SC₂H₅ | CH₃ | |
| Cl | H | H | SC₂H₅ | CH₃ | |
| SO₂CH₃ | H | H | SC₂H₅ | C₂H₅ | |
| SO₂N(CH₃)₂ | H | H | SC₂H₅ | C₂H₅ | |
| CO₂CH₃ | CH₃ | H | SC₂H₅ | C₂H₅ | |
| CO₂CH₃ | H | 5-OCH₃ | SC₂H₅ | CH₃ | |
| CO₂CH₃ | H | H | SCH₂CH₂CH₃ | H | |
| NO₂ | H | H | SCH₂CH₂CH₃ | H | |
| SO₂CF₃ | H | H | SCH₂CH₂CH₃ | CH₃ | |
| CO₂CH₃ | H | H | SCH(CH₃)₂ | H | |
| NO₂ | CH₃ | H | SCH(CH₃)₂ | H | |
| CO₂CH₃ | H | 5-CH₃ | SCH(CH₃)₂ | CH₃ | |

TABLE IV

Structure: naphthalene with SO₂NHC(O)NR group, linked to triazine N-oxide with X, Y substituents; R₃ on naphthalene.

| R₃ | R | X | Y | m.p. (°C.) |
|---|---|---|---|---|
| H | H | CH₃ | H | |
| CH₃ | H | CH₃ | H | |
| CH₂CH₃ | H | CH₃ | H | |
| CH(CH₃)₂ | H | CH₃ | H | |
| OCH₃ | H | CH₃ | H | |
| OCH₂CH₃ | H | CH₃ | H | |
| OCH(CH₃)₂ | H | CH₃ | H | |
| Cl | H | CH₃ | H | |
| OSO₂CH₃ | H | CH₃ | H | |
| SO₂CH₃ | H | CH₃ | H | |
| H | H | OCH₃ | H | |
| CH₃ | H | OCH₃ | H | |
| CH₂CH₃ | H | OCH₃ | H | |
| CH(CH₃)₂ | H | OCH₃ | H | |
| OCH₃ | H | OCH₃ | H | |
| OCH₂CH₃ | H | OCH₃ | H | |
| OCH(CH₃)₂ | H | OCH₃ | H | |
| Cl | H | OCH₃ | H | |
| OSO₂CH₃ | H | OCH₃ | H | |
| SO₂CH₃ | H | OCH₃ | H | |

TABLE V

Structure: thiophene (R₅ substituted) with SO₂NHC(O)NR group linked to triazine N-oxide.

| R₅ | R | X | Y | m.p. (°C.) |
|---|---|---|---|---|
| H | H | CH₃ | H | |
| CH₃ | H | CH₃ | H | |
| Cl | H | CH₃ | H | |
| Br | H | CH₃ | H | |
| NO₂ | H | CH₃ | H | |
| SO₂CH₃ | H | CH₃ | H | |
| SO₂N(CH₃)₂ | H | CH₃ | H | |
| CO₂CH₃ | H | CH₃ | H | |
| H | H | OCH₃ | H | |
| CH₃ | H | OCH₃ | H | |
| Cl | H | OCH₃ | H | |
| Br | H | OCH₃ | H | |
| NO₂ | H | OCH₃ | H | |
| SO₂CH₃ | H | OCH₃ | H | |
| SO₂N(CH₃)₂ | H | OCH₃ | H | |
| CO₂CH₃ | H | OCH₃ | H | |

TABLE VI

Structure: thiophene (R₅ substituted) with SO₂NHC(O)NR group linked to triazine N-oxide.

| R₅ | R | X | Y | m.p. (°C.) |
|---|---|---|---|---|
| H | H | CH₃ | H | |
| CH₃ | H | CH₃ | H | |
| Cl | H | CH₃ | H | |
| Br | H | CH₃ | H | |
| NO₂ | H | CH₃ | H | |
| SO₂CH₃ | H | CH₃ | H | |
| SO₂N(CH₃)₂ | H | CH₃ | H | |
| CO₂CH₃ | H | CH₃ | H | |
| H | H | OCH₃ | H | |
| CH₃ | H | OCH₃ | H | |
| Cl | H | OCH₃ | H | |
| Br | H | OCH₃ | H | |
| NO₂ | H | OCH₃ | H | |
| SO₂CH₃ | H | OCH₃ | H | |
| SO₂N(CH₃)₂ | H | OCH₃ | H | |
| CO₂CH₃ | H | OCH₃ | H | |

TABLE VII

Structure: pyridine (R₄ substituted) with SO₂NHC(O)NR group linked to triazine N-oxide.

| R₄ | R | X | Y | m.p. (°C.) |
|---|---|---|---|---|
| H | H | CH₃ | H | |
| CH₃ | H | CH₃ | H | |
| OCH₃ | H | CH₃ | H | |
| Cl | H | CH₃ | H | |
| SO₂CH₃ | H | CH₃ | H | |
| SO₂N(CH₃)₂ | H | CH₃ | H | |
| H | H | OCH₃ | H | |
| CH₃ | H | OCH₃ | H | |
| OCH₃ | H | OCH₃ | H | |
| Cl | H | OCH₃ | H | |
| SO₂CH₃ | H | OCH₃ | H | |
| SO₂N(CH₃)₂ | H | OCH₃ | H | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE IV

| | Weight Percent* | | |
|---|---|---|---|
| | Active Ingredient | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley & Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 3

Wettable Powder

N-[(5-methyl-1,2,4-triazin-3-yl)aminocarbonyl]-2-(methylsulfonyloxy)benzenesulfonamide, 1-oxide—80%
sodium alkylnaphthalenesulfonate—2%
sodium lignisulfonate—2%
synthetic amorphous silica—3%
kaolinite—13%

The ingredients are blended, hammer-milled until all the solids are essentially under 50 microns, reblended, and packaged.

EXAMPLE 4

Wettable Powder

N-[(5-methyl-1,2,4-triazin-3-yl)aminocarbonyl]-2-propoxybenzenesulfonamide, 1-oxide—50%
sodium alkylnaphthalenesulfonate—2%
low viscosity methyl cellulose—2%
diatomaceous earth—46%

The ingredients are blended, coarsely hammermilled and then air-milled to produce particles essentially all below 10 microns in diameter. The product is reblended before packaging.

EXAMPLE 5

Granule

Wettable Powder of Example 4—5%
attapulgite granules (U.S.S. 20-40 mesh; 0.84-0.42 mm)—95%

A slurry of wettable powder containing $\approx 25\%$ solids is sprayed on the surface of attapulgite granules in a double-cone blender. The granules are dried and packaged.

EXAMPLE 6

Extruded Pellet

N',N'-dimethyl-N-[(5-methyl-1,2,4-triazin-3-yl)aminocarbonyl]-1,2-benzenedisulfonamide, 1-oxide—25%
anhydrous sodium sulfate—10%
crude calcium lignisulfonate—5%
sodium alkylnaphthalenesulfonate—1%
calcium/magnesium bentonite—59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 7

Oil Suspension

2-[(5-methyl-1,2,4-triazin-3-yl)aminocarbonyl]aminosulfonyl]benzoic acid, methyl ester, 1-oxide—25%
polyoxyethylene sorbitol hexaoleate—5% highly aliphatic hydrocarbon oil—70%

The ingredients are ground together in a sand mill until the solid particles have been reduced to under about 5 microns. The resulting thick suspension may be applied directly, but preferably after being extended with oils or emulsified in water.

EXAMPLE 8

Wettable Powder

N-[(5-methyl-1,2,4-triazin-3-yl)aminocarbonyl]-2-nitrobenzenesulfonamide, 1-oxide—20%
sodium alkylnaphthalenesulfonate—4%
sodium ligninsulfonate—4%
low viscosity methyl cellulose—3%
attapulgite—69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 9

Low Strength Granule

N',N'-dimethyl-N-[(5-methyl-1,2,4-triazin-3-yl)aminocarbonyl]-1,2-benzenedisulfonamide, 1-oxide—1%
N,N-dimethylformamide—9%
attapulgite granules (U.S.S. 20–40 sieve)—90%

The active ingredient is dissolved in the solvent and the solution is sprayed upon dedusted granules in a double cone blender. After spraying of the solution has been completed, the blender is allowed to run for a short period and then the granules are packaged.

EXAMPLE 10

Aqueous Suspension

N-[(5-methyl-1,2,4-triazin-3-yl)aminocarbonyl]-2-chlorobenzenesulfonamide, 1-oxide—40%
polyacrylic acid thickener—0.3%
dodecylphenol polyethylene glycol ether—0.5%
disodium phosphate—1%
monosodium phosphate—0.5%
polyvinyl alcohol—1.0%
water—56.7%

The ingredients are blended and ground together in a sand mill to produce particles essentially all under 5 microns in size.

EXAMPLE 11

Solution

N-[(5-methyl-1,2,4-triazin-3-yl)aminocarbonyl]-2-propoxybenzenesulfonamide, 1-oxide, sodium salt—5%
water—95%

The salt is added directly to the water with stirring to produce the solution, which may then be packaged for use.

EXAMPLE 12

Low Strength Granule

N-[(5-methyl-1,2,4-triazin-3-yl)aminocarbonyl]-2-(methylsulfonyloxy)benzenesulfonamide, 1-oxide—0.1%
attapulgite granules (U.S.S. 20–40 mesh)—99.9%

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 13

Granule

N-[(5-methyl-1,2,4-triazin-3-yl)aminocarbonyl]-2-nitrobenzenesulfonamide, 1-oxide—80%
wetting agent—1%
crude lignisulfonate salt (containing 5–20% of the natural sugars)—10%
attapulgite clay—9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 14

High Strength Concentrate

N-[(5-methyl-1,2,4-triazin-3-yl)aminocarbonyl]-2-chlorobenzenesulfonamide, 1-oxide—99%
silica aerogel—0.5%
synthetic amorphous silica—0.5%

The ingredients are blended and ground in a hammer-mill to produce a material essentially all passing a U.S.S. No. 50 screen (0.3 mm opening). The concentrate may be formulated further if necessary.

EXAMPLE 15

Wettable Powder

2-[(5-methyl-1,2,4-triazin-3-yl)aminocarbonyl]-aminosulfonyl]benzoic acid, methyl ester, 1-oxide 90%
dioctyl sodium sulfosuccinate—0.1%
synthetic fine silica—9.9%

The ingredients are blended and ground in a hammer-mill to produce particles essentially all below 100 microns. The material is sifted through a U.S.S. No. 50 screen and then packaged.

EXAMPLE 16

Wettable Powder

2-[(5-methyl-1,2,4-triazin-3-yl)aminocarbonyl]-aminosulfonyl]benzoic acid, methyl ester, 1-oxide—40%
sodium ligninsulfonate—20%
montmorillonite clay—40%

The ingredients are thoroughly blended, coarsely hammer-milled and then air-milled to produce particles essentially all below 10 microns in size. The material is reblended and then packaged.

EXAMPLE 17

Oil Suspension

N',N'-dimethyl-N-[(5-methyl-1,2,4-triazin-3-yl)aminocarbonyl]-1,2-benzenedisulfonamide, 1-oxide—35% blend of polyalcohol carboxylic esters and oil soluble petroleum sulfonates—6%
xylene—59%

The ingredients are combined and ground together in a sand mill to produce particles essentially all below 5 microns. The product can be used directly, extended with oils, or emulsified in water.

EXAMPLE 18
Dust

N-[(5-methyl-1,2,4-triazin-3-yl)aminocarbonyl]-2-chlorobenzenesulfonamide, 1-oxide—10%
attapulgite—10%
Pyrophyllite—80%

The active ingredient is blended with attapulgite and then passed through a hammer-mill to produce particles substantially all below 200 microns. The ground concentrate is then blended with powdered pyrophyllite until homogeneous.

Utility

The compounds of the present invention are highly active herbicides. They have utility for broadspectrum pre- and/or post-emergence weed control in areas where complete control of all vegetation is desired, such as around fuel storage tanks, ammunition depots, industrial storage areas, parking lots, drivein theaters, around billboards, highway and railroad structures.

The rates of application for the compounds of the invention are determined by a number of factors, including the types of weeds to be controlled, weather and climate, formulations selected, mode of application, amount of foliage present, etc. In general terms, the subject compounds should be applied at levels of around 0.01 to 5 kg/ha, the lower rates being suggested for use on lighter soils and/or those having a low organic matter content, or for situations where only short-term persistence is required.

The compounds of the invention may be used in combination with any other commercial herbicide examples of which are those of the triazine, triazole, uracil, urea, amide, diphenylether, carbamate and bipyridylium types.

The herbicidal properties of the subject compounds were discovered in a number of greenhouse tests. The test procedure and results follow.

Test A

Seeds of crabgrass (Digitaria sp.), barnyardgrass (Echinochloa crusgalli), wild oats (Avena fatua), sicklepod (Cassia obtusifolia), morningglory (Ipomoea sp.), cocklebur (Xanthium pensylvanicum), sorghum, corn, soybean, sugar beet, rice, wheat and nutsedge tubers (Cyperus rotundus) were planted and treated pre-emergence with the chemicals dissolved in a non-phytotoxic solvent. At the same time, these crop and weed species, along with cotton and bush bean, were treated with a soil/foilage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
E=emergence inhibition;
G=growth retardation;
H=formative effects;
U=unusual pigmentation; and
6Y=abscised buds or flowers.

The data indicate that the compounds tested are highly active pre- and/or post-emergence herbicides because of the low rates of applications selected for this test.

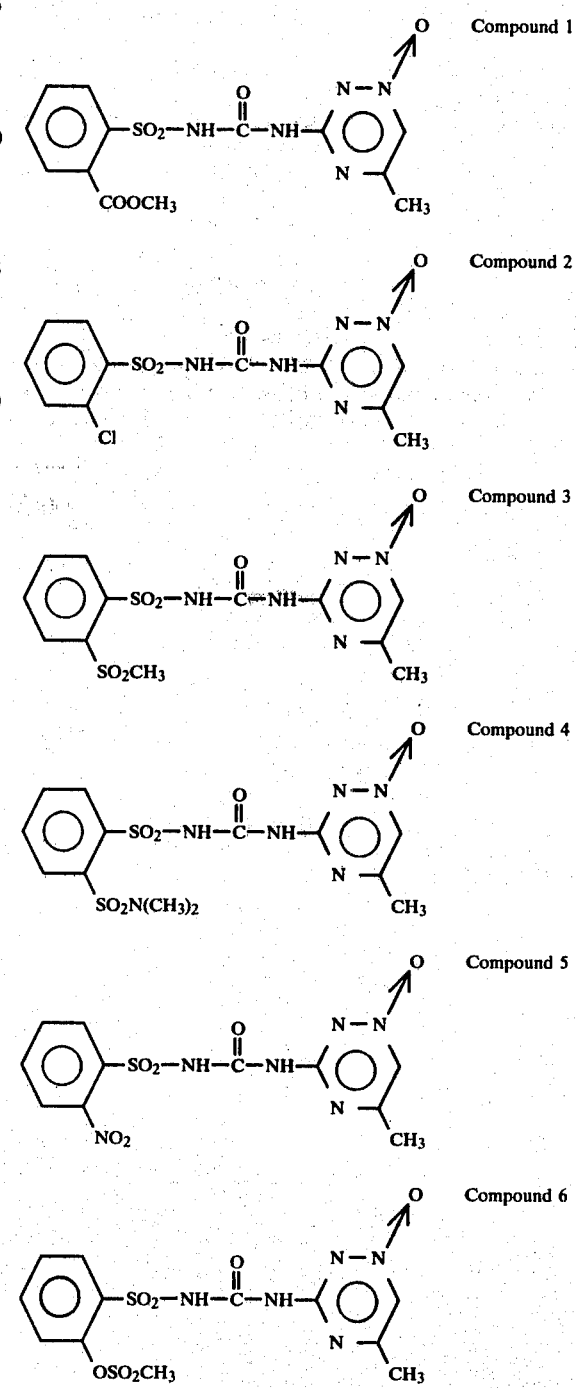

Table A Compounds

TABLE A

| | Compound 1 | | Compound 2 | | Compound 3 | | Compound 4 | |
|---|---|---|---|---|---|---|---|---|
| Rate kg/ha | .04 | 2 | .04 | 2 | .04 | 2 | .04 | 2 |
| POST-EMERGENCE | | | | | | | | |
| Bush bean | 6C,9G,6Y | 9C | 4C,9G,6Y | 9C | 0 | 9C | 4C,9G,6Y | 9C |
| Cotton | 4C,9G | 5C,9G | 2C,4G | 5C,9G | 0 | 4C,9H | 4C,8H | 9C |
| Morningglory | 4C,8G | 9C | 4C,8H | 5C,9G | 0 | 4C,8H | 3C,9G | 10C |
| Cocklebur | 2C,8H | 9C | 3G | 9C | 0 | 3C,9G | 6H | 10C |
| Sicklepod | 4C,7H | 9C | 3C,4H | 9C | 0 | 4C,9H | 3C | 5C,9G |
| Nutsedge | 3C,8G | 9C | 5G | 4C,9G | 0 | 3C,9G | 0 | 4C,9G |
| Crabgrass | 2C | 6C,9G | 1C,4H | 3C,9G | 0 | 2C,7G | 3C,7G | 9C |
| Barnyardgrass | 9C | 9C | 4C,9H | 9C | 1H | 9C | 9C | 9C |
| Wild Oats | 5C,9G | 9C | 2C,5G | 9C | 0 | 9C | 9C | 9C |
| Wheat | 4C,9G | 5U,9C | 1C,5G | 4C,9G | 2C,6G | 9C | 9C | 10C |
| Corn | 4C,9H | 6U,9C | 2U,9G | 8U,9C | 1C | 7U,9C | 2C,9H | 9C |
| Soybean | 4C,9G | 6C,9G | 3C,8G,5X | 6C,9G | 0 | 5C,9G | 5C,9G | 9C |
| Rice | 5C,9G | 9C | 3C,9G | 6C,9G | 1C,7G | 6C,9G | 9C | 9C |
| Sorghum | 5U,9G | 10C | 2C,9G | 5U,9G | 2C | 5C,9G | 4U,9G | 10C |
| Sugar beet | 4C,8G | 9C | 4C,9H | 5C,9G | 0 | 4C,9G | 9C | 9C |
| PRE-EMERGENCE | | | | | | | | |
| Morningglory | 3C,8H | 9C | 3C,7H | 10C | 0 | 1C | 3C,7H | 9C |
| Cocklebur | 9H | 9H | 4G | 9H | 0 | 9H | 9H | 9H |
| Sicklepod | 4C,7G | 9C | 3C,8G | 9C | 0 | 2C,8G | 2C,7G | 9G |
| Nutsedge | 2C,9G | 10E | 0 | 10E | 0 | 10E | 10E | 10E |
| Crabgrass | 1C | 2C,8G | 2G | 3C,8G | 0 | 1C | 2C | 5C,8G |
| Barnyardgrass | 2C,5G | 5C,9H | 2C,2H | 10H | 0 | 4C,7H | 4C,8H | 5C,9H |
| Wild Oats | 2C,5G | 5C,9H | 2C,7G | 5C,9H | 0 | 3C,8G | 3C,8G | 5C,9G |
| Wheat | 2C,8H | 10H | 2C,9G | 10E | 0 | 9H | 4C,9H | 10H |
| Corn | 2C,8H | 10E | 2C,9G | 10E | 0 | 9G | 9H | 9H |
| Soybean | 3C,5H | 9H | 2C,3H | 8H | 0 | 2C,4H | 4C,6H | 9H |
| Rice | 10E | 10E | 10E | 10E | 0 | 10E | 5C,9H | 10E |
| Sorghum | 4C,9H | 10H | 2C,9H | 10H | 0 | 4C,9H | 5C,9H | 5C,9H |
| Sugar beet | 7G | 10E | 2C,8H | 10E | 0 | 1C | 5G | 5C,9G |

| | Compound 5 | | Compound 6 | | Compound 7 | |
|---|---|---|---|---|---|---|
| Rate kg/ha | .04 | 2 | .04 | 2 | .04 | 2 |
| POST-EMERGENCE | | | | | | |
| Bush bean | 4C,9G,6Y | 6C,9G,6Y | 4C,4G,6Y | 6C,9G,6Y | 5C,9G,6Y | 9C |
| Cotton | 2C | 4C,9G | 0 | 6C,9G | 5C,9G | 4C,9G |
| Morningglory | 3C,8G | 3C,9G | 2C,4G | 5C,9G | 4C,9G | 9C |
| Cocklebur | 2C,8H | 10C | 2G | 4C,9H | 10C | 9C |
| Sicklepod | 2C,3G | 3C,8H | 2C | 4C,8G | 2C,5G | 2C,8G |
| Nutsedge | 2C,8G | 4C,9G | 0 | 2C,6G | 2C,9G | 5C,9G |
| Crabgrass | 1C,3G | 4C,9G | 0 | 3C,8G | 2C,8G | 4C,9G |
| Barnyardgrass | 5C,9H | 9C | 0 | 9C | 2C,9H | 9C |
| Wild Oats | 2C,7G | 6C,9G | 0 | 5C,9G | 2C,8G | 5C,9G |
| Wheat | 3C,9G | 6C,9G | 1C,3G | 2C,9G | 2C,4G | 2C,9G |
| Corn | 4U,9G | 9C | 2C,7H | 7U,9G | 1C,3G | 2U,9G |
| Soybean | 3C,9G | 5C,9G | 1C,3G | 5C,9G | 5C,9G | 5C,9G |
| Rice | 5C,9G | 5C,9G | 2C,6G | 6C,9G | 4C,9G | 5C,9G |
| Sorghum | 2C,7G | 3U,9G | 0 | 2U,9G | 2C,9H | 2U,9G |
| Sugar beet | 2C,8G | 9C | 4G | 9C | 9C | 9C |
| PRE-EMERGENCE | | | | | | |
| Morningglory | 1C,3G | 9G | 2C,2H | 4C,5H | 9C | 5C,9G |
| Cocklebur | 9H | 9H | 0 | 3C,9H | 9H | 9H |
| Sicklepod | 6G | 9G | 0 | 2C,9G | 7G | 9G |
| Nutsedge | 10E | 10E | 0 | 10E | 10E | 10E |
| Crabgrass | 0 | 3C,9G | 0 | 1C | 2C,4G | 5C,9G |
| Barnyardgrass | 2C,5H | 3C,9H | 0 | 3C,8H | 4C,9H | 5C,9H |
| Wild Oats | 2C,7G | 5C,9H | 0 | 8G | 2C,8G | 5C,9H |
| Wheat | 2C,9G | 10H | 0 | 8G | 5G | 5C,9H |
| Corn | 2C,8H | 10E | 2C,3G | 2C,9G | 2C,9G | 2C,9H |
| Soybean | 2C,2H | 8H | 1C | 3C,3H | 4C,8H | 9H |
| Rice | 10E | 10E | 2C | 10E | 3C,9H | 10E |
| Sorghum | 2C,7H | 5C,9H | 0 | 3C,7H | 3C,9H | 10H |
| Sugar beet | 8G | 10E | 2C,4G | 5C,9G | 4C,9G | 5C,9G |

-continued
Table A Compounds

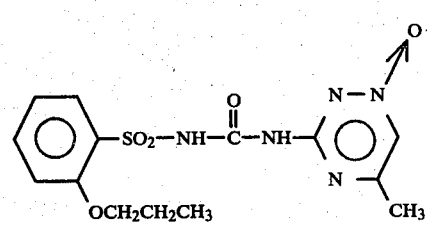

Compound 7

What is claimed is:
1. A compound of the formula:

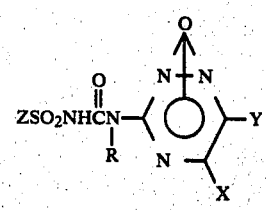

wherein
Z is

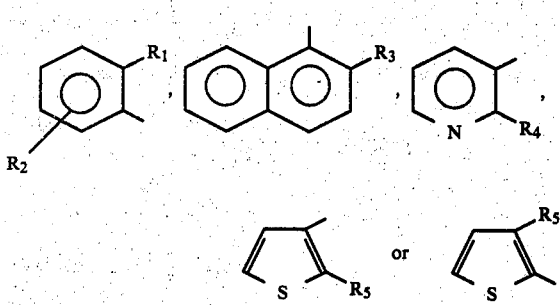

R is H or $CH_3$;
$R_1$ is $CO_2R_6$, $S(O)_nR_7$, $OSO_2R_8$, $OR_9$, $SO_2NR_{10}R_{11}$, $SO_2N(OCH_3)CH_3$, $CH_2OR_{12}$, F, Cl, Br, $NO_2$, $CF_3$ or $C_1$–$C_4$ alkyl;
$R_2$ is F, Cl, Br, $NO_2$, $CF_3$, $CH_3$, $OCH_3$ or H;
$R_3$ is H, $C_1$–$C_3$ alkyl, $C_1$–$C_3$ alkoxy, Cl, $OSO_2CH_3$ or $SO_2R_8$;
$R_4$ is H, $CH_3$, $OCH_3$, Cl, $SO_2CH_3$ or $SO_2N(CH_3)_2$;
$R_5$ is H, $CH_3$, Cl, Br, $NO_2$, $SO_2CH_3$, $SO_2N(CH_3)_2$ or $CO_2R_8$;
$R_6$ is $C_1$–$C_4$ alkyl, $CH_2CH=CH_2$, $CH_2CH_2OCH_3$ or $CH_2CH_2Cl$;
$R_7$ is $C_1$–$C_3$ alkyl, $CH_2CH=CH_2$, $CF_3$, $CF_2H$ or $CF_2CF_2H$;
$R_8$ is $C_1$–$C_3$ alkyl;
$R_9$ is $C_1$–$C_4$ alkyl, $C_3$–$C_4$ alkenyl, $CF_3$, $CF_2H$ or $CF_2CF_2H$;
$R_{10}$ and $R_{11}$ are independently $C_1$–$C_3$ alkyl;
$R_{12}$ is $C_1$–$C_2$ alkyl;
n is 0, 1 or 2;
X is H, $C_1$–$C_3$ alkyl, $C_1$–$C_3$ alkoxy, Cl, Br, $C_1$–$C_3$ thioalkyl or $N(CH_3)_2$; and
Y is H, Cl, Br, $CH_3$ or $C_2H_5$; and their agriculturally suitable salts; provided that the total number of carbon atoms in $R_{10}$ and $R_{11}$ are less than or equal to 4.

2. Compounds of claim 1 where the N-oxide is in the 1-position; Y is H or $CH_3$; and R is H.

3. Compounds of claim 2 where

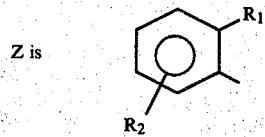

4. Compounds of claim 3 where $R_1$ is $CO_2R_6$, $SO_2NR_{10}R_{11}$, $NO_2$, Cl, $C_1$–$C_3$ alkyl or $C_1$–$C_3$ alkoxy.

5. The compound of claim 1 which is 2-[5-methyl-1,2,4-triazin-3-yl)aminocarbonyl]aminosulfonyl]benzoic acid, methyl ester, 1-oxide.

6. The compound of claim 1 which is N-[(5-methyl-1,2,4-triazin-3-yl)aminocarbonyl]-2-chlorobenzenesulfonamide, 1-oxide.

7. The compound of claim 1 which is N',N'-dimethyl-N-[(5-methyl-1,2,4-triazin-3-yl)aminocarbonyl]-1,2-benzenedisulfonamide, 1-oxide.

8. The compound of claim 1 which is N-[(5-methyl-1,2,4-triazin-3-yl)aminocarbonyl]-2-nitrobenzenesulfonamide, 1-oxide.

9. The compound of claim 1 which is N-[(5-methyl-1,2,4-triazin-3-yl)aminocarbonyl]-2-(methylsulfonyloxy)benzenesulfonamide, 1-oxide.

10. The compound of claim 1 which is N-[(5-methyl-1,2,4-triazin-3-yl)aminocarbonyl]-2-propoxybenzenesulfonamide, 1-oxide.

11. A composition suitable for controlling the growth of undesired vegetation which comprises an effective amount of a compound of claim 1 and at least one of the following: surfactant, solid or liquid diluent.

12. A composition suitable for controlling the growth of undesired vegetation which comprises an effective amount of a compound of claim 2 and at least one of the following: surfactant, solid or liquid diluent.

13. A composition suitable for controlling the growth of undesired vegetation which comprises an effective amount of a compound of claim 3 and at least one of the following: surfactant, solid or liquid diluent.

14. A composition suitable for controlling the growth of undesired vegetation which comprises an effective amount of a compound of claim 4 and at least one of the following: surfactant, solid or liquid diluent.

15. A composition suitable for controlling the growth of undesired vegetation which comprises an effective amount of the compound of claim 5 and at least one of the following: surfactant, solid or liquid diluent.

16. A composition suitable for controlling the growth of undesired vegetation which comprises an effective amount of the compound of claim 6 and at least one of the following: surfactant, solid or liquid diluent.

17. A composition suitable for controlling the growth of undesired vegetation which comprises an effective amount of the compound of claim 7 and at least one of the following: surfactant, solid or liquid diluent.

18. A composition suitable for controlling the growth of undesired vegetation which comprises an effective amount of the compound of claim 8 and at least one of the following: surfactant, solid or liquid diluent.

19. A composition suitable for controlling the growth of undesired vegetation which comprises an effective amount of the compound of claim 9 and at least one of the following: surfactant, solid or liquid diluent.

20. A composition suitable for controlling the growth of undesired vegetation which comprises an effective amount of the compound of claim 10 and at least one of the following: surfactant, solid or liquid diluent.

21. A method for controlling the growth of undesired vegetation which comprises applying to the locus to be protected an effective amount of a compound of claim 1.

22. A method for controlling the growth of undesired vegetation which comprises applying to the locus to be protected an effective amount of a compound of claim 2.

23. A method for controlling the growth of undesired vegetation which comprises applying to the locus to be protected an effective amount of a compound of claim 3.

24. A method for controlling the growth of undesired vegetation which comprises applying to the locus to be protected an effective amount of a compound of claim 4.

25. A method for controlling the growth of undesired vegetation which comprises applying to the locus to be protected an effective amount of the compound of claim 5.

26. A method for controlling the growth of undesired vegetation which comprises applying to the locus to be protected an effective amount of the compound of claim 6.

27. A method for controlling the growth of undesired vegetation which comprises applying to the locus to be protected an effective amount of the compound of claim 7.

28. A method for controlling the growth of undesired vegetation which comprises applying to the locus to be protected an effective amount of the compound of claim 8.

29. A method for controlling the growth of undesired vegetation which comprises applying to the locus to be protected an effective amount of the compound of claim 9.

30. A method for controlling the growth of undesired vegetation which comprises applying to the locus to be protected an effective amount of the compound of claim 10.

* * * * *